US010370717B2

(12) United States Patent
Maheshwari et al.

(10) Patent No.: US 10,370,717 B2
(45) Date of Patent: Aug. 6, 2019

(54) METHODS FOR THE MEASUREMENT OF POST-TRAUMATIC STRESS DISORDER MICRORNA MARKERS

(71) Applicant: The Henry M. Jackson Foundation for the Advancement of Military Medicine, Inc., Bethesda, MD (US)

(72) Inventors: Radha K. Maheshwari, Rockville, MD (US); Nagaraja S. Balakathiresan, Clarksburg, MD (US); Manish Bhomia, Rockville, MD (US); Raghavendar Chandran, Rockville, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 93 days.

(21) Appl. No.: 15/306,178

(22) PCT Filed: Apr. 21, 2015

(86) PCT No.: PCT/US2015/026956
§ 371 (c)(1),
(2) Date: Oct. 24, 2016

(87) PCT Pub. No.: WO2015/164431
PCT Pub. Date: Oct. 29, 2015

(65) Prior Publication Data
US 2017/0044613 A1  Feb. 16, 2017

Related U.S. Application Data

(60) Provisional application No. 61/982,651, filed on Apr. 22, 2014.

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2014/0073516 A1 | 3/2014 | Hood et al. | |
|---|---|---|---|
| 2014/0256562 A1* | 9/2014 | Umansky | C12Q 1/6883 506/2 |

FOREIGN PATENT DOCUMENTS

| WO | 2006/033020 A2 | 3/2006 |
| WO | 2013/018060 A2 | 2/2013 |

OTHER PUBLICATIONS

Free Dictionary definition of "Measuring" available via url: < thefreedictionary.com/measuring>, printed on Sep. 20, 2017.*
Balakathiresan et al J Neurotrauma. May 2012. 29: 1379-1387 and Supplementary Data.*
MiRBase entry for MI0000074 / hsa-mir-19b-1, printed on Jul. 2, 2018, available via URL: <mirbase.org/cgi-bin/mirna_entry.pl?acc=MI0000074>.*
MiRBase entry for MI0000298 / has-mir-221, printed on Jul. 2, 2018, available via URL: <mirbase.org/cgi-bin/mirna_entry.pl?acc=MI0000298>.*
MiRBase entry for MI0000300 / has-mir-223 (printed on Jul. 2, 2018, available via URL: < mirbase.org/cgi-bin/mirna_entry.pl?acc=MI0000300>.*
Alderfer et al J Head Trauma. 2005. 20(6): 544-562.*
Redell et al J of Neurotrauma. Dec. 2010. 27: Supplemental Table 2.*
Pasinetti et al Am J Neurodegener Disease. 2012. 1(1): 88-98.*
International Search Report and Written Opinion issued in the corresponding International Application No. PCT/US2015/026956 dated Mar. 30, 2016.
Lei et al., "Microarray based analysis of microRNA expression in rat cerebral cortex after traumatic brain injury," Brain Research, doi:10.1016/j.brainres.2009.05.074 (2009).
Mondello et al., "Blood-based diagnostics of traumatic brain injuries," Expert Rev. Mol. Diagn.,11(1): 65-78 (2011).
Balakathiresan et al., "MicroRNA Let-7i Is a Promising Serum Biomarker for Blast-Induced Traumatic Brain Injury," J. Neurotrauma, 29(7): 1379-1387 (2012).
Hu et al. "Expression of miRNAs and their cooperative regulation of the pathophysiology in traumatic brain injury," PLoS ONE, 7(6):e39357 (2012).
Redell et al., "Traumatic Brain Injury Alters Expression of Hippocampal MicroRNAs: Potential Regulators of Multiple Pathophysiological Processes," Journal of Neuroscience Research, 87:1435-1448 (2009).
Guo et al., "The Fate of miRNA* Strand through Evolutionary Analysis: Implication for Degradation as Merely Carrier Strand or Potential Regulatory Molecule?" PLoS ONE, 5(6): e11387 (2010).
TaqMan Array MicroRNA Cards, TaqMan OpenArray MicroRNA Plates and Megaplex Primer Pools (Date: Mar. 18, 2014) [online] [retrieved on Sep. 23, 2015] Retrieved from Thermofisher.com, 60 pages <https://www.thermofisher.com/order/catalog/product/4398967> + TaqMan Rodent MicroRNA A Array v2.0 [online], [retrieved on Sep. 23, 2015] Retrieved from Thermofisher.com, 2 pages <https://www.thermofisher.com/order/catalog/product/4398967>.

(Continued)

*Primary Examiner* — Carla J Myers
(74) *Attorney, Agent, or Firm* — Morgan, Lewis & Bockius LLP

(57) ABSTRACT

The present invention provides for methods of measuring levels of micro RNAs for the diagnosis, treatment and/or monitoring the progression of post-traumatic stress disorder (PTSD) or traumatic brain injury (TBI) in a subject having or suspected of having PTSD and/or TBI. The methods, in general comprise measuring levels of at least one of miR-142-5p, miR-19b, miR-1928, miR-223-3p, miR-322*, miR-324, miR-421-3p, miR-463* and miR-674* is a sample from a subject suffering from or suspected of having PTSD and/or TBI.

7 Claims, 15 Drawing Sheets

Specification includes a Sequence Listing.

(56) References Cited

OTHER PUBLICATIONS

Balakathiresan et al., "Serum and amygdala microRNA signatures of posttraumatic stress: fear correlation and biomarker potential," J. Psychiatr. Res., 57:65-73 (2014).
Cho et al. (2014) Molecular evidence of stress-induced acute heart injury in a mouse model simulating posttraumatic stress disorder, PNAS, 111:3188-3193.
Lei et al. (2009) Microarray based analysis of microRNA expression in rat cerebral cortex after traumatic brain injury, Brain Res., 1284:191-201.
Redell et al. (2010) Human traumatic brain injury alters plasma microRNA levels, J. Neurotrauma, 27:2147-2156.
Schmidt et al. (2013) Therapeutic action of fluoxetine is associated with a reduction in prefontal cortical MiR-1971 expression levels in a mouse model of posttraumatic stress disorder, Front Psychiatry, 4:66.

* cited by examiner

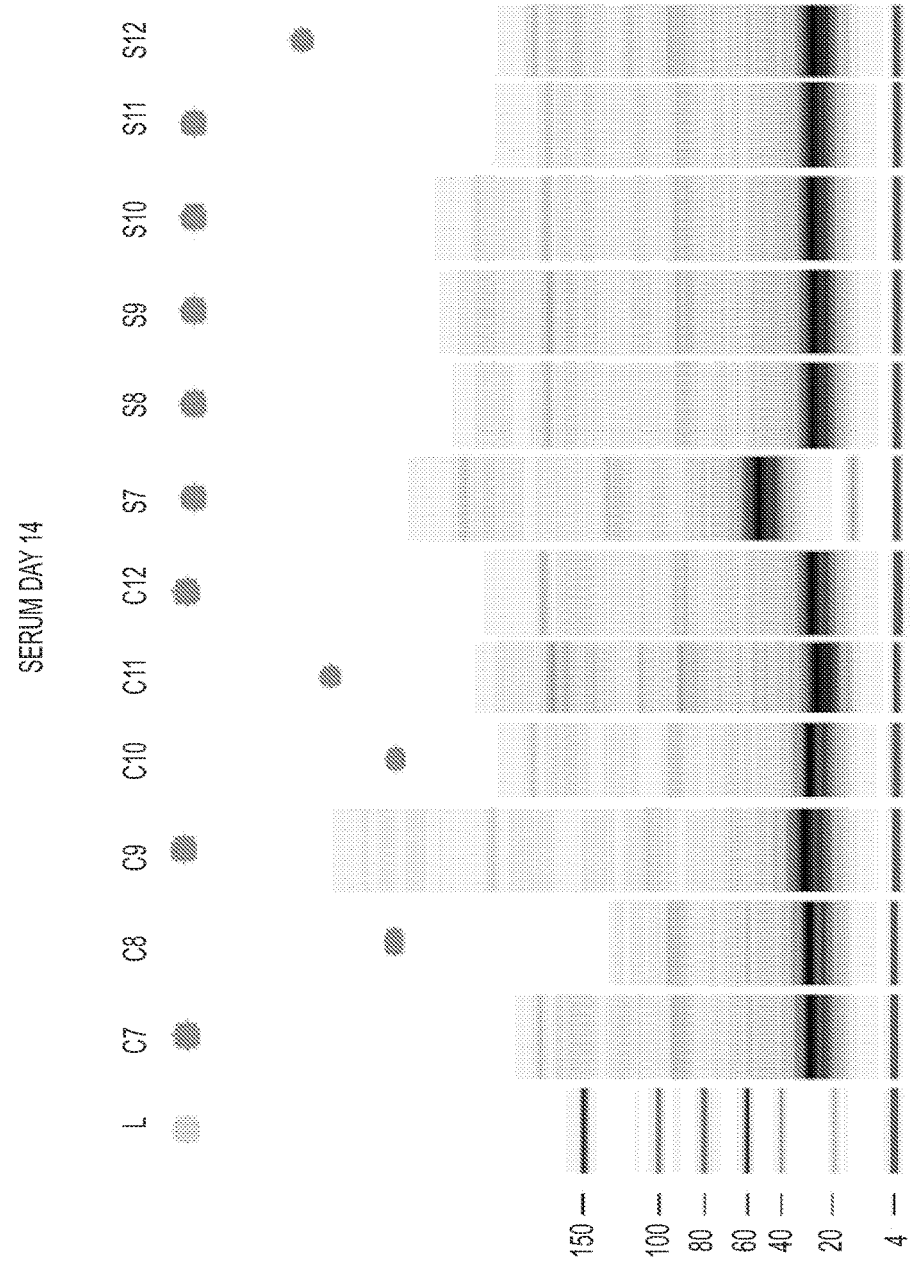

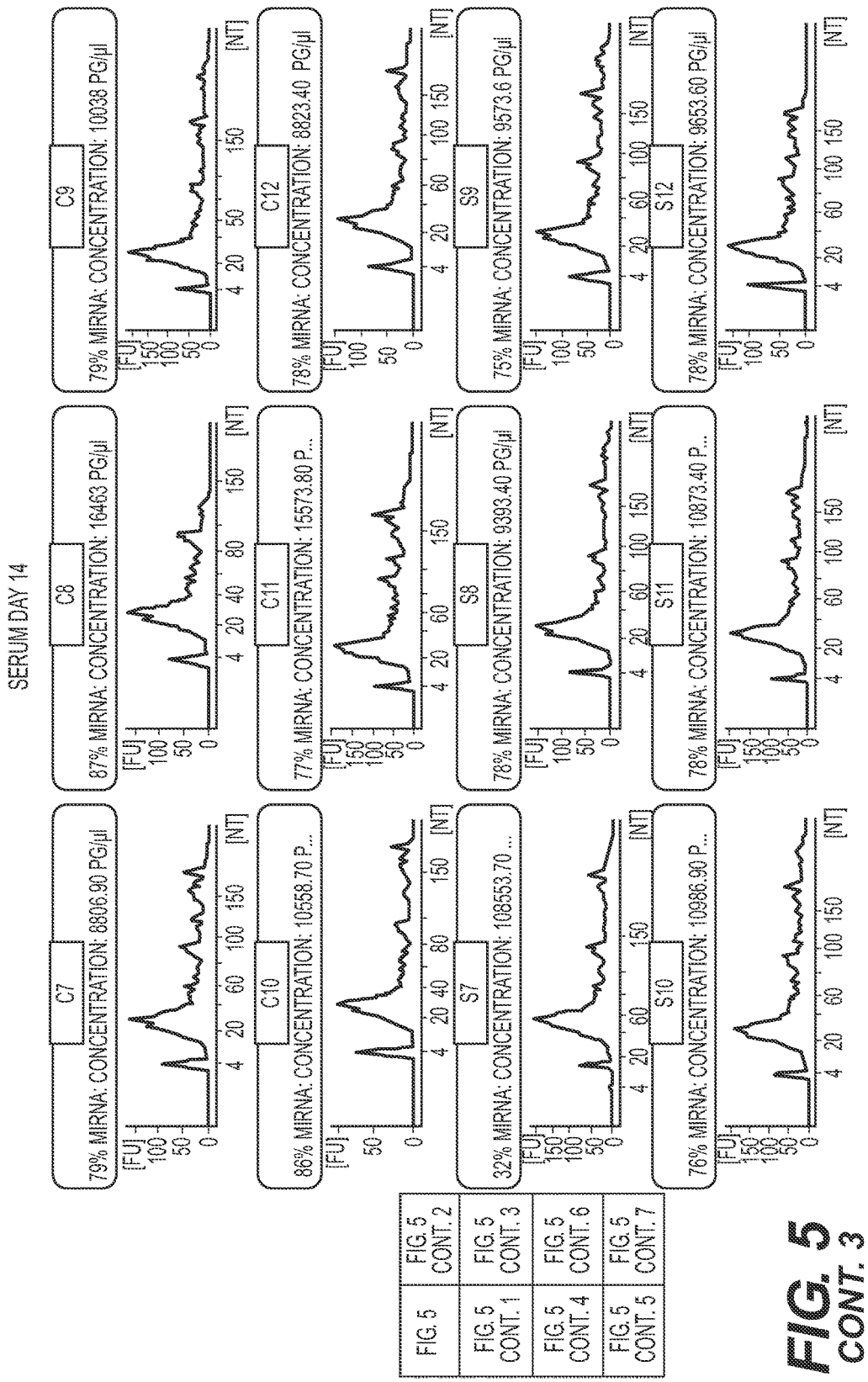

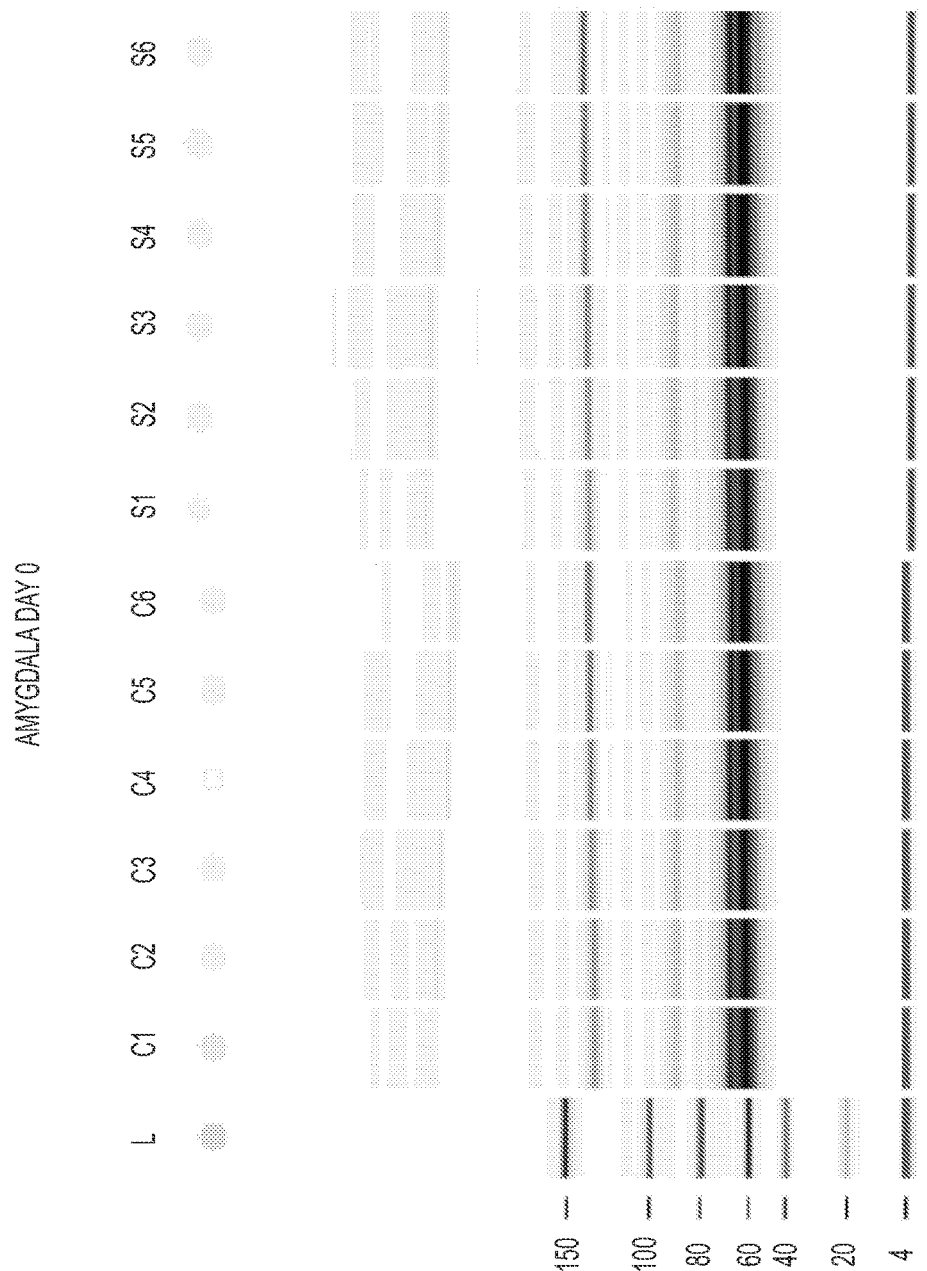

SEQUENCE LISTING

```
<160> NUMBER OF SEQ ID NOS: 9

<210> SEQ ID NO 1
<211> LENGTH: 21
<212> TYPE: RNA
<213> ORGANISM: Artificial Sequence
<220> FEATURE:
<223> OTHER INFORMATION: Synthetic (micro RNA biomarker)

<400> SEQUENCE: 1
cauaaaguag aaagcacuac u                                             21

<210> SEQ ID NO 2
<211> LENGTH: 23
<212> TYPE: RNA
<213> ORGANISM: Artificial Sequence
<220> FEATURE:
<223> OTHER INFORMATION: Synthetic (micro RNA biomarker)
```

<400> SEQUENCE: 2
ugugcaaauc caugcaaaac uga                                           23

<210> SEQ ID NO 3
<211> LENGTH: 23
<212> TYPE: RNA
<213> ORGANISM: Artificial Sequence
<220> FEATURE:
<223> OTHER INFORMATION: Synthetic (micro RNA biomarker)

<400> SEQUENCE: 3
agcuacauug ucugcugggu uuc                                           23

<210> SEQ ID NO 4
<211> LENGTH: 21
<212> TYPE: RNA
<213> ORGANISM: Artificial Sequence
<220> FEATURE:
<223> OTHER INFORMATION: Synthetic (micro RNA biomarker)

<400> SEQUENCE: 4
ugucaguuug ucaaauaccc c                                             21

<210> SEQ ID NO 5
<211> LENGTH: 20
<212> TYPE: RNA
<213> ORGANISM: Artificial Sequence
<220> FEATURE:
<223> OTHER INFORMATION: Synthetic (micro RNA biomarker)

<400> SEQUENCE: 5
aaacaugaag cgcugcaaca                                               20

<210> SEQ ID NO 6
<211> LENGTH: 22
<212> TYPE: RNA
<213> ORGANISM: Artificial Sequence
<220> FEATURE:
<223> OTHER INFORMATION: Synthetic (micro RNA biomarker)

<400> SEQUENCE: 6
ccacugcccc aggugcugcu gg                                            22

<210> SEQ ID NO 7
<211> LENGTH: 20
<212> TYPE: RNA
<213> ORGANISM: Artificial Sequence
<220> FEATURE:
<223> OTHER INFORMATION: Synthetic (micro RNA biomarker)

<400> SEQUENCE: 7
aucaacagac auuaauuggg                                               20

<210> SEQ ID NO 8
<211> LENGTH: 21
<212> TYPE: RNA
<213> ORGANISM: Artificial Sequence
<220> FEATURE:
<223> OTHER INFORMATION: Synthetic (micro RNA biomarker)

<400> SEQUENCE: 8
uaccuaauuu guuguccauc a                                             21

<210> SEQ ID NO 9

```
-continued

<211> LENGTH: 22
<212> TYPE: RNA
<213> ORGANISM: Artificial Sequence
<220> FEATURE:
<223> OTHER INFORMATION: Synthetic (micro RNA biomarker)

<400> SEQUENCE: 9
cacagcuccc aucucagaac aa                                            22
```

METHODS FOR THE MEASUREMENT OF POST-TRAUMATIC STRESS DISORDER MICRORNA MARKERS

CROSS-REFERENCE TO RELATED APPLICATIONS

The present application claims priority of U.S. Provisional patent application No. 61/982,651 filed on Apr. 22, 2014, the entire contents of which are incorporated herein by reference.

GOVERNMENT SUPPORT

This invention was made with government support under HT9404-13-1-0003 awarded by the Uniformed Services University of the Health Sciences. The government has certain rights in the invention

SEQUENCE LISTING SUBMISSION VIA EFS-WEB

A computer readable text file, entitled "044508-5050-SequenceListing.txt," created on or about 24 Oct. 2016 with a file size of about 2.4 kb contains the sequence listing for this application and is hereby incorporated by reference in its entirety.

FIELD OF THE INVENTION

The present invention relates in general to the reliable detection and identification of biomarkers produced in subjects suffering from post-traumatic stress disorder (PTSD). Inventive markers include DNA, RNA, or microRNA (μRNA) that may play a role in central nervous system function and therapy. In particular the invention relates to processes and kits for the detection and measurement of PTSD, μRNA biomarkers and administration of therapeutics for patients suffering from the disorder. In addition, the invention provides for an in vitro diagnostic device which enables the reliable detection and identification of biomarkers, important for the diagnosis and prognosis of PTSD and to serve as objective surrogate endpoints for therapy.

BACKGROUND OF THE INVENTION

Post-Traumatic Stress Disorder (PTSD) affects 7-8% of the general population of the United States and approximately 15% of veterans returning from combat. The symptoms can persist for months or decades. Unfortunately, PTSD is often misdiagnosed and left untreated in affected civilian and military individuals, disrupting the quality of their lives, their families and children, as well as our healthcare system.

PTSD is a severely disabling anxiety disorder which can occur after mild traumatic brain injury (TBI), a subject has seen or experienced a traumatic event that involved the threat of injury or death and which can be found clinically in acute or chronic forms. Relevant traumatic experiences include experiencing or witnessing childhood abuse, vehicle accidents, medical complications, physical assaults, natural disasters, jail, or war. The symptoms of PTSD include, but are not limited to, intrusion of recurrent nightmares or daytime flashbacks, characterized by high anxiety, hyper-arousal, which is a constant jumpy preparation for fight or flight and avoidance of contact with anything or anyone that might remind the patient of the trauma. Acute PTSD may resolve within 3-6 months, whereas chronic PTSD is a waxing and waning disorder that can persist for months, years, or decades. PTSD is often co-morbid with other psychiatric disorders, such as, but not limited to, depression, substance abuse, and suicidal thoughts.

Current diagnosis of PTSD is established on the basis of clinical history and subjective mental status examination, using a clinically structured interview, symptom checklists, or patient self-reports. These subjective tests, however, make it difficult to distinguish PTSD from other psychiatric disorders, resulting in difficult treatment decisions as to both treatment interventions and a more definitive understanding of the etiology. The existing limitations of current clinical assessment would benefit substantially from a more objective means to enhance the ability to identify PTSD in a patient and thus enabling the ability to differentiate PTSD from other psychiatric disorders in patients.

Treatments for PTSD include but are not limited to psychotherapy, such as but not limited to Cognitive Behavioral Therapy, pharmacotherapy, such as but not limited to serotonin-specific reuptake inhibitor (SSRI's). Many different pharmacological approaches have been investigated. For example, it is believed that Major Depressive Disorder (MDD) and PTSD have much in common, thus antidepressants, such as but not limited to the SSRI drugs fluoxitine (Prozac) and paroxatine (Paxil) are widely considered effective at treating some symptoms of PTSD. Other commonly administered SSRI antidepressants have included venlafaxine (Effexor) and sertraline (Zoloft).

Other commonly administered antipsychotics used to treat PTSD include but are not limited to mirtazapine (Remeron), olanzapine (Zyprexa) and quetiapione (Seroquel). The beta blocker propranolol has also been used to try to block memory formation in PTSD patients. Prazosin, an $\alpha_1$-selective adrenoceptor antagonist, has been reported to reduce trauma-related nightmares and sleep disturbances associated with PTSD.

Because PTSD can only be diagnosed through a personal interview of a patient, where the patient may be cognizant to give answers they know to be correct, the current methods leave it difficult to diagnose subjects suffering from these disorders. As a result, a majority of PTSD cases are often missed, misdiagnosed or left untreated in thousands of affected individuals. To date there are no clinical methods for diagnosing PTSD because of the lack of reliability, specificity and cost efficacy.

Biomarkers are increasingly used to diagnose diseases promptly and accurately, and to identify individuals at high risk for certain conditions and tendencies even before clinical manifestations arise. There are presently no biomarkers to validate the diagnosis or to serve as objective surrogate endpoints for therapy for PTSD.

Micro RNAs (μRNAs) are small (~22 nucleotides) non-coding RNAs that can be posttranscriptional gene regulators for diverse biological processes. In circulation, μRNAs are considered as good biomarkers because they are highly stable in serum. Currently, however, there are no reports on the use of circulatory μRNAs as non-invasive biomarkers for the diagnosis of PTSD.

Despite today's technology with biomarker analysis, there remains an unmet need for prognostic indicators that can aid in the objective detection PTSD. In addition, there exists a need for a method of diagnosing PTSD, a need to monitor PTSD progression, a need for detecting PTSD prior to the onset of detectable symptoms and a need for clinical intervention with therapeutics. Finally, there remains for an unmet need for an in vitro diagnostic device to identify neurochemical markers to detect and/or diagnose PTSD.

SUMMARY OF THE INVENTION

A process for measuring for an amount of µRNA biomarkers is provided for the clinical evaluation of the levels of biomarkers of at least one of miR-142-5p, miR-19b, miR-1928, miR-223-3p, miR-322*, miR-324, miR-421-3p, miR-463* and miR-674*. In at least one embodiment, the invention is directed to clinical evaluation of the levels of biomarkers of mir-19b-3p, mir-223-3p and mir-421-3p. In one embodiment, the methods include obtaining at least one biological sample from a subject suspecting of having or being at risk of suffering from post-traumatic stress disorder (PTSD) or traumatic brain injury (TBI). In another embodiment, assessing levels of biomarker comprises the use of agents that specifically hybridize to each µRNA for quantitative PCR using amplification, hybridization, and/or sequencing methods.

The inventive process utilizes biological samples obtained at least thirteen days after a subject has been exposed to traumatic event likely to cause PTSD or TBI. In at least one embodiment a biological sample is obtained within one week after the subject presents with clinical symptoms of PTSD or TBI. In at least one embodiment, the biological samples are obtained within 24 hours after the subject presents with clinical symptoms of PTSD or TBI. In another embodiment, the biological samples are obtained within 24 hours after the subject experiences a traumatic episode. In at least one embodiment, exemplar biological samples include whole blood, plasma, serum, CSF, urine, saliva, sweat, prefrontal cortex tissue, hippocampus tissue, or ipsilateral cortex tissue.

In some embodiments of the inventive process, a therapeutic agent is administered to a subject and an additional biological sample is obtained some time after the therapeutic has been administered and the biological sample is measured for the RNA biomarkers. In some embodiments, the therapeutic may be administered if the quantities of the measured biomarkers are modulated with respect to an amount present in a normal control, or modulated with respect to the amounts measured in a historical biological sample of the subject, where the historical biological sample was taken from the subject at some time prior to the subject experiencing the traumatic event or receiving the traumatic brain injury. In at least one embodiment the therapeutic is an antidepressant, an antipsychotic, or combinations thereof. Exemplar antidepressant and antipsychotic therapeutics include fluoxitine (Prozac) and paroxatine (Paxil), venlafaxine (Effexor), sertraline (Zoloft), mirtazapine (Remeron), olanzapine (Zyprexa) and quetiapione (Seroquel), propranolol, or an $\alpha_1$-selective adrenoceptor antagonist (Prazosin), or combinations thereof. In other embodiments, the administered therapeutic agent may be a therapeutically effective amount of a pharmaceutical composition including a pharmaceutically acceptable salt or ester for the treatment of PTSD or TBI, which may further include an anti-depressant or an antipsychotic.

In at least one embodiment successive biological samples are collected as a function of time, i.e., a sample is obtained at a second, third, fourth, etc. time point, and the biomarkers are measured in each sample to monitor for a change in the amount of the biomarkers present in the subject over time.

Other embodiments include a process of determining the presence of a post-traumatic stress disorder (PTSD) or traumatic brain injury (TBI) in a subject. These embodiments include collecting a biological sample from an affected subject suspected of suspected of having PTSD or TBI or presenting with clinical symptoms of PTSD or TBI, and measuring levels of at least one micro RNA (biomarker) selected from miR-142-5p, miR-19b, miR-1928, miR-223-3p, miR-322*, miR-324, miR-421-3p, miR-463*, miR-674*, and combinations thereof, and comparing the amount of the biomarker with a normal levels of the at least one micro RNA Once the levels of the one or more micro RNAs have been determined, this determination can then be compared to normal levels or baseline levels of the one or more micro RNAs. "Normal levels" of the micro RNA may be assessed by measuring levels of the micro RNA in a known healthy subject, including the same subject that is later screened or being diagnosed. Normal levels may also be assessed over a population sample, where a population sample is intended to mean either multiple samples from a single subject or at least one sample from a multitude of subjects. The samples used to generate the population can be taken from previously harvested tissues that, for example, may be stored in paraffin or cryogenically stored. The population of samples can continually grow as additional samples are added to the population to gain statistical confidence in the data. Normal levels of the micro RNA, in terms of a population of samples, may or may not be categorized according to characteristics of the population including, but not limited to, sex, age, weight, ethnicity, geographic location, fasting state, state of pregnancy or post-pregnancy, menstrual cycle, general health of the subject, alcohol or drug consumption, caffeine or nicotine intake and circadian rhythms.

The invention is not limited by the means by which the biomarker micro RNAs are assessed. The assessment of the levels of the individual biomarkers can be expressed as absolute or relative values, such as but not limited to a concentration, and may or may not be expressed in relation to another component, such as a standard an internal standard or another molecule of compound known to be in the sample, such as but not limited to a ratio. If the levels are assessed as relative to a standard or internal standard, the standard may be added to the test sample prior to, during or after sample processing.

Of course, measurements of the individual biomarkers, e.g., concentration, can fall within a range of values, and values that do not fall within this "normal range" are said to be outside the normal range. These measurements may or may not be converted to a value, number, factor or score as compared to measurements in the "normal range." For example, a measurement for a specific micro RNA that is below the normal range, may be assigned a value or −1, −2, −3, etc., depending on the scoring system devised.

In one embodiment, the collection of micro RNAs can be used to generate a "micro RNA profile value." The profile can be a single value, number, factor or score given as an overall collective value to the individual components of the profile. For example, if each of the components is assigned a value, such as above, the profile value may simply be the overall score of each individual value. For example, if 9 components are used to generate the micro RNA profile and five of the components are assigned values of "−2" and four are assigned values of "−1," the micro RNA profile value in this example would be −14, with a normal value being "0." In this manner, the micro RNA profile value could be useful single number or score, the actual value or magnitude of which could be an indication of the actual risk of PTSD, e.g., the "more negative" the value, the greater the risk of suffering from PTSD.

Some embodiments include a kit to assist with the process of obtaining a biological sample and measuring for the amounts of the RNA biomarkers described herein. In at least one embodiment, the kit includes a substrate for holding a biological sample isolated from a human subject and an agent which specifically hybridizes to the micro RNA. In at least one embodiment the micro RNA the kit also includes printed instructions for reacting the agent with the sample or a portion of the sample to detect the presence or amount of the biomarker. In at least one embodiment, the amount of the measured biomarker is used for diagnosing the PTSD or TBI in the subject from whom the biological sample was obtained. In at least one embodiment the level of a micro RNA is detected using amplification, hybridization, and/or sequencing methods (e.g., quantitative PCR).

Further embodiments include an in vitro diagnostic device for measuring certain biomarkers. In some embodiments the in vitro diagnostic device is used for detecting PTSD or TBI in a subject. The inventive in vitro diagnostic devices include at least one sample chamber for holding a biological sample collected from the subject and an assay module in fluid communication with the sample chamber. In at least one embodiment the in vitro diagnostic device includes a power supply. In at least one embodiment an inventive in vitro diagnostic device includes a data processing module in operable communication with the power supply and the assay module where the assay module analyzes the biological sample to detect at least one of the biomarkers associated with PTSD or TBI present in the biological sample and electronically communicates a presence of the biomarker detected in the first biological sample to said data processing module to be displayed on an output. In at least one embodiment the data processing module has an output that relates to detecting the PTSD or TBI in the subject, the output being the amount of the biomarker measured, the presence or absence of PTSD or TBI, or the severity of PTSD or TBI. In some embodiments the output is a display in electrical communication with the data processing module communicating the output as an amount of the PTSD or TBI biomarker measured, a comparison between the amount of PTSD or TBI and a normal control or historical control, the presence of PTSD or TBI, or the severity of PTSD or TBI. In some embodiments, the in vitro diagnostic device includes a transmitter for communicating the output to a remote location. In an alternative embodiment, the in vitro diagnostic device includes a handheld sample chamber for holding a biological sample from the subject, an assay module in fluid communication with said sample chamber, and a dye providing a colorimetric change in response to at least one measured PTSD or TBI biomarker present in the biological sample.

BRIEF DESCRIPTION OF THE DRAWINGS

FIG. 3A illustrates the top 10 functional pathways of posttraumatic stress altered day 14 serum and amygdala common micro RNAs and their validated targets from miR Walk database using Ingenuity pathway analysis program. While

DETAILED DESCRIPTION OF THE PREFERRED EMBODIMENTS

Figure 1:
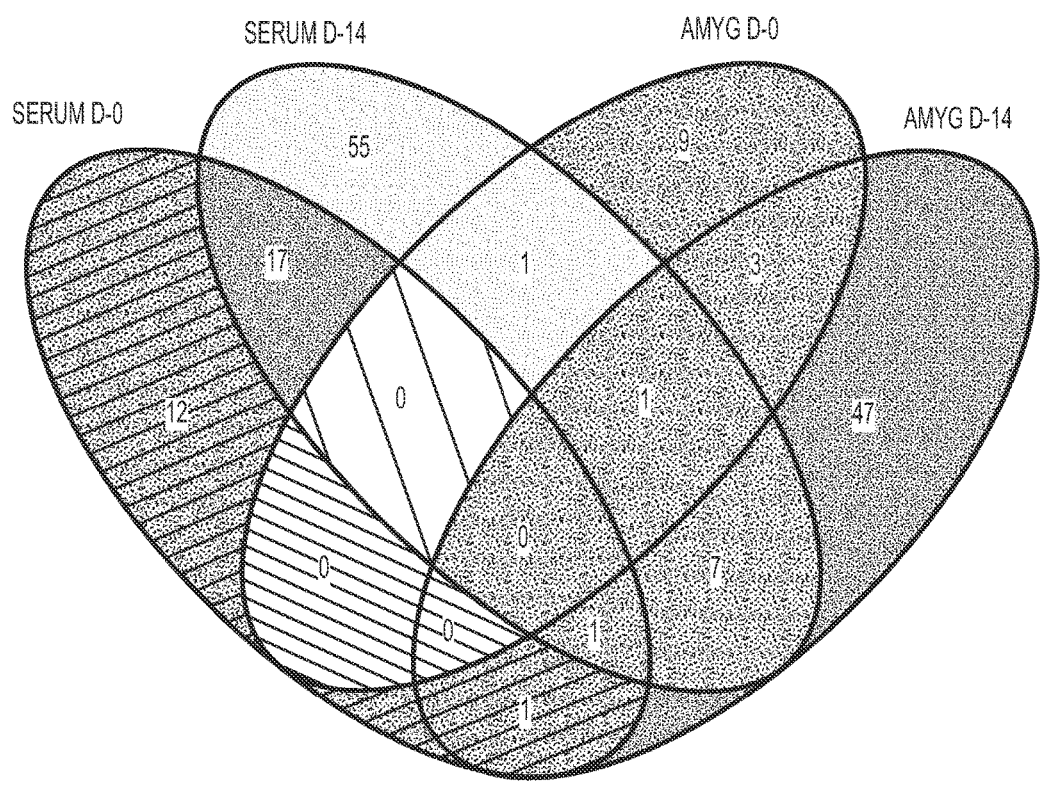
FIG. 1 illustrates the validation of miR-223 expression in amygdala and serum samples of day 14. The levels of micro RNA were normalized by the level of MammU6 endogenous control RNA, and all reactions were performed in triplicate.

The present invention has utility as processes, devices and biomarkers neural injuries, disorders and psychiatric or behavioral disorders such as PTSD and TBI thereby allowing for clinical intervention. The invention may further be used to detect neural injuries or neuronal disorders which the provided neural protein biomarkers may be comorbid.

The following detailed description is merely exemplary in nature and is in no way intended to limit the scope of the invention, its application, or uses, which may vary. The invention is described with relation to the non-limiting definitions and terminology included herein. These definitions and terminology are not designed to function as a limitation on the scope or practice of the invention, but are presented for illustrative and descriptive purposes only. Various terms used throughout the specification and claims are defined as set forth below as it may be helpful to an understanding of the invention.

"Marker" in the context of the present invention refers to Nucleic acids including micro RNA (μRNA), protein or breakdown product (BDP) or an antibody to one of the aforementioned that thereof is differentially present in a sample taken from patients having neural injury and/or psychiatric disorders as compared to a comparable sample taken from control subjects (e.g., a person with a negative diagnosis, normal or healthy subject) or from a historical value of the marker for the patient.

A "breakdown product" is defined as a fragment of a micro RNA or protein that is detectable and of sufficient size to correlate to the base micro RNA or protein.

The phrase "psychiatric disorder" is used herein in the broadest sense, and indicates a mental disorder that interferes with the way a person behaves, interacts with others, and functions in daily life. The Diagnostic and Statistical Manual (DSM) of Mental Disorders, published by the American Psychiatric Association, classifies psychiatric disorders such as PTSD, MDD, BP and SCZ.

The term "traumatic episode" refers to, with or without temporary or permanent injury, a near death experience, criminal assault, rape, natural disasters, serious accidents, combat exposure, child physical or sexual abuse or severe neglect, witnessing the death or destruction of someone or something, being exposed to events causing elevated levels of fear for a person's life or the lives of others, imprisonment/hostage/displacement as refugees, torture, or the sudden unexpected death of loved ones.

The terms "patient," "individual" or "subject" are used interchangeably herein, and is meant a mammalian subject to be treated, with human patients being one specific embodiment. In some cases, the processes of the invention find use in experimental animals, in veterinary application, and in the development of vertebrate models for disease, including, but not limited to, rodents including mice, rats, and hamsters; birds, fish reptiles, and primates.

The term "normal subject" refers to a mammalian subject, such as a human patient, that is not or has not suffered from neural injury manifest in psychiatric terms and does not have a history of past neural injuries or any psychiatric disorders.

The term "normal amount" refers to the amount of biomarkers measured from a normal subject.

The term "historical sample" refers to a biological sample taken from a subject prior to the exposure to a traumatic event, or prior to the manifestation of clinical symptoms of neural injuries or any psychiatric disorders.

The term "historical amount" refers to the amount of biomarkers measured from a historical sample.

"Biological Sample" is used herein includes polynucleotides, polypeptides, peptides, antibodies fragments and correlatable breakdown products and is a bodily fluid, a soluble fraction of a cell preparation, or media in which cells are grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint; skin; or hair; and fragments of the aforementioned.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Immunoassay" is an assay that uses an antibody to specifically bind an antigen or an antigen to bind an antibody (e.g., a marker). The immunoassay is characterized by the use of specific binding properties of a particular antibody to isolate, target, and/or quantify the antigen. It should be appreciated that many immunoassays exist and could be used interchangeably with this invention.

As used herein, the term "Traumatic Brain Injury" or "TBI" is art recognized and is intended to include the condition in which, a traumatic blow to the head causes damage to the brain, often without penetrating the skull. Usually, the initial trauma can result in expanding hematoma, subarachnoid hemorrhage, cerebral edema, raised intracranial pressure (ICP), and cerebral hypoxia, which can, in turn, lead to severe secondary events due to low cerebral blood flow (CBF). Depending upon severity, TBI may also be classified as severe, mild or moderate.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised against marker NF-200 from specific species such as rat, mouse, or human can be selected to obtain only those polyclonal antibodies that are specifically immunoreactive with marker NF-200 and not with other proteins, except for polymorphic variants and alleles of marker NF-200. This selection may be achieved by subtracting out antibodies that cross-react with marker NF-200 molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

As used herein, the term "in vitro diagnostic" means any form of diagnostic test product or test service, including but not limited to a FDA approved, or cleared, In Vitro Diagnostic (IVD), Laboratory Developed Test (LDT), or Direct-to-Consumer (DTC), that may be used to assay a sample and detect or indicate the presence of, the predisposition to, or the risk of, diseases, disorders, conditions, infections and/or therapeutic responses. In one embodiment, an in vitro diagnostic may be used in a laboratory or other health professional setting. In another embodiment, an in vitro diagnostic may be used by a consumer at home. In vitro diagnostic test comprise those reagents, instruments, and systems intended for use in the in vitro diagnosis of disease or other conditions, including a determination of the state of health, in order to cure, mitigate, treat, or prevent disease or its sequelae. In one embodiment in vitro diagnostic products may be intended for use in the collection, preparation, and examination of specimens taken from the human body. In certain embodiments, in vitro diagnostic tests and products may comprise one or more laboratory tests such as one or more in vitro diagnostic tests. As used herein, the term "laboratory test" means one or more medical or laboratory procedures that involve testing samples of blood, serum, plasma, CSF, sweat, saliva or urine, buccal sample or other human tissues or substances.

A nucleic acid probe or primer able to hybridize to a target biomarker micro RNA or is used for detecting and/or quantifying micro RNA encoding a biomarker protein for PTSD. A nucleic acid probe can be an oligonucleotide of at least 10, 15, 30, 50 or 100 nucleotides in length and sufficient to specifically hybridize under stringent conditions to the biomarker protein micro RNA or complementary sequence thereof. A nucleic acid primer can be an oligonucleotide of at least 10, 15 or 20 nucleotides in length and sufficient to specifically hybridize under stringent conditions to the micro RNA, or complementary sequence thereof.

"Complement" and "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

"Hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art.

"Stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and P. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

"Specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing Denhardt's solution and related chemistry such as 30% formamide incubated at 37° C. overnight followed by conventional washing.

PTSD and TBI Biomarker Processes

A process for measuring for an amount of micro RNA biomarkers is provided for the simultaneous clinical evaluation of the levels of biomarkers of miR-142-5p, miR-19b, miR-1928, miR-223-3p, miR-322*, miR-324, miR-421-3p, miR-463* and miR-674*. It should be appreciated that additional markers selected from Tables 1-3, illustrated herein, are also suitable micro RNA candidates and may be used in addition to, or as a substitution of any of the aforementioned micro RNAs. In at least one embodiment simultaneous clinical evaluation of the levels of biomarkers of miR-19b-3p, miR-223-3p and miR-221-3p is provided. In another embodiment measuring for the quantity of at least one micro RNA biomarker selected from miR-142-5p, miR-19b, miR-1928, miR-223-3p, miR-322*, miR-324, miR-421-3p, miR-463* and miR-674* is provided. In some embodiments the process includes the administration of a therapeutic agent after a biological sample is obtained from a subject presenting with symptoms of PTSD or TBI. Measurements of the biomarkers are accomplished by obtaining at least one biological sample at a first time point from a subject presenting with clinical symptoms of a post-traumatic stress disorder (PTSD) or traumatic brain injury (TBI). In at least one embodiment measurement of the biomarkers is accomplished by using an agent which specifically hybridizes to each micro RNA on a quantitative PCR using amplification, hybridization, and/or sequencing methods.

The inventive process utilizes biological samples obtained at least thirteen days after a subject has been exposed to traumatic event likely to cause PTSD or TBI. In at least one embodiment a biological sample is obtained within one week after the subject presents with clinical symptoms of PTSD or TBI. In another embodiment, the sample is obtained after one week that the subject exhibits clinical symptoms of PTSD and/or TBI. In at least one embodiment, the biological samples are obtained within 24 hours after the subject presents with clinical symptoms of PTSD or TBI. In another embodiment, the biological samples are obtained within 24 hours after the subject experiences a traumatic episode. In at least one embodiment at least two biological samples are taken from a subject after presenting with clinical symptoms of PTSD or TBI. In some embodiments the at least two samples are obtained within 24 hours of the subjects clinical presence, while in other embodiments the at least two samples are obtained within two weeks of the subjects clinical presence. Exemplar biological samples for practicing the inventive process include whole blood, plasma, serum, CSF, urine, saliva, sweat, prefrontal cortex tissue, hippocampus tissue, or ipsilateral cortex tissue. It is appreciated that several methods exist for obtaining the aforementioned biological samples and are well known in the art and incorporated herein.

In some embodiments of the inventive process, a therapeutic agent is administered to a subject and an additional biological sample is obtained some time after the therapeutic has been administered and the biological sample is measured for the micro RNA biomarkers. In some embodiments, the therapeutic may be administered if the quantities of the measured biomarkers are modulated with respect to an amount present in a normal control, or modulated with respect to the amounts measured in a historical biological sample of the subject, where the historical biological sample was taken from the subject at some time prior to the subject experiencing the traumatic event or receiving the traumatic brain injury.

In at least one embodiment the therapeutic is an antidepressant, an antipsychotic, or combinations thereof. Exemplar antidepressant and antipsychotic therapeutics include fluoxitine (Prozac) and paroxatine (Paxil), venlafaxine (Effexor), sertraline (Zoloft), mirtazapine (Remeron), olanzapine (Zyprexa) and quetiapione (Seroquel), propranolol, or an al-selective adrenoceptor antagonist (Prazosin), or combinations thereof. In other embodiments, the administered therapeutic may be a therapeutically effective amount of a pharmaceutical composition including a pharmaceutically acceptable salt or ester for the treatment of PTSD or TBI, which may further include an anti-depressant or an antipsychotic.

Other embodiments include a process of determining the presence of a post-traumatic stress disorder (PTSD) or traumatic brain injury (TBI) in a subject. These embodiments include collecting a biological sample at a first time point from an affected subject suspected of having PTSD or TBI or presenting with clinical symptoms of PTSD or TBI, measuring the biological sample for an amount of at least one biomarker selected from miR-142-5p, miR-19b, miR-1928, miR-223-3p, miR-322*, miR-324, miR-421-3p, miR-463* and miR-674*, or combinations thereof, and comparing the amount of the biomarker with a normal amount of the biomarker measured in a normal subject not having PTSD or TBI. In at least one embodiment the measured levels of biomarkers in the affected subject are compared with a historical amount of the biomarkers measured in a historical biological sample from the subject prior to the subject being affected with the PTSD or TBI. Differential between the measured amount of biomarkers from the affected subject when compared to the normal levels or the historical levels is indicative of PTSD or TBI in the affected subject. In at least one embodiment, a plurality of markers are measured selected from the group consisting of miR-142-5p, miR-19b, miR-1928, miR-223-3p, miR-322*, miR-324, miR-421-3p, miR-463* and miR-674*. In at least one embodiment, the biomarkers miR-19b-3p, miR-223-3p and miR-221-3p are measured from the same sample and compared with normal amounts and/or historical amounts.

In additional embodiments, biological samples are collected and analyzed at least at a second time point to monitor the progression of PTSD and TBI in the subject over time.

In other embodiments, a therapeutic agent is administered to treat the PTSD or TBI and biological samples are collected and analyzed at least at a second time point to monitor the effectiveness of the therapeutic agent in treating PTSD and TBI in the subject over time. In at least one embodiment the μRNAs are detected by Northern blot.

In Vitro Diagnostic Device

Figure 8:
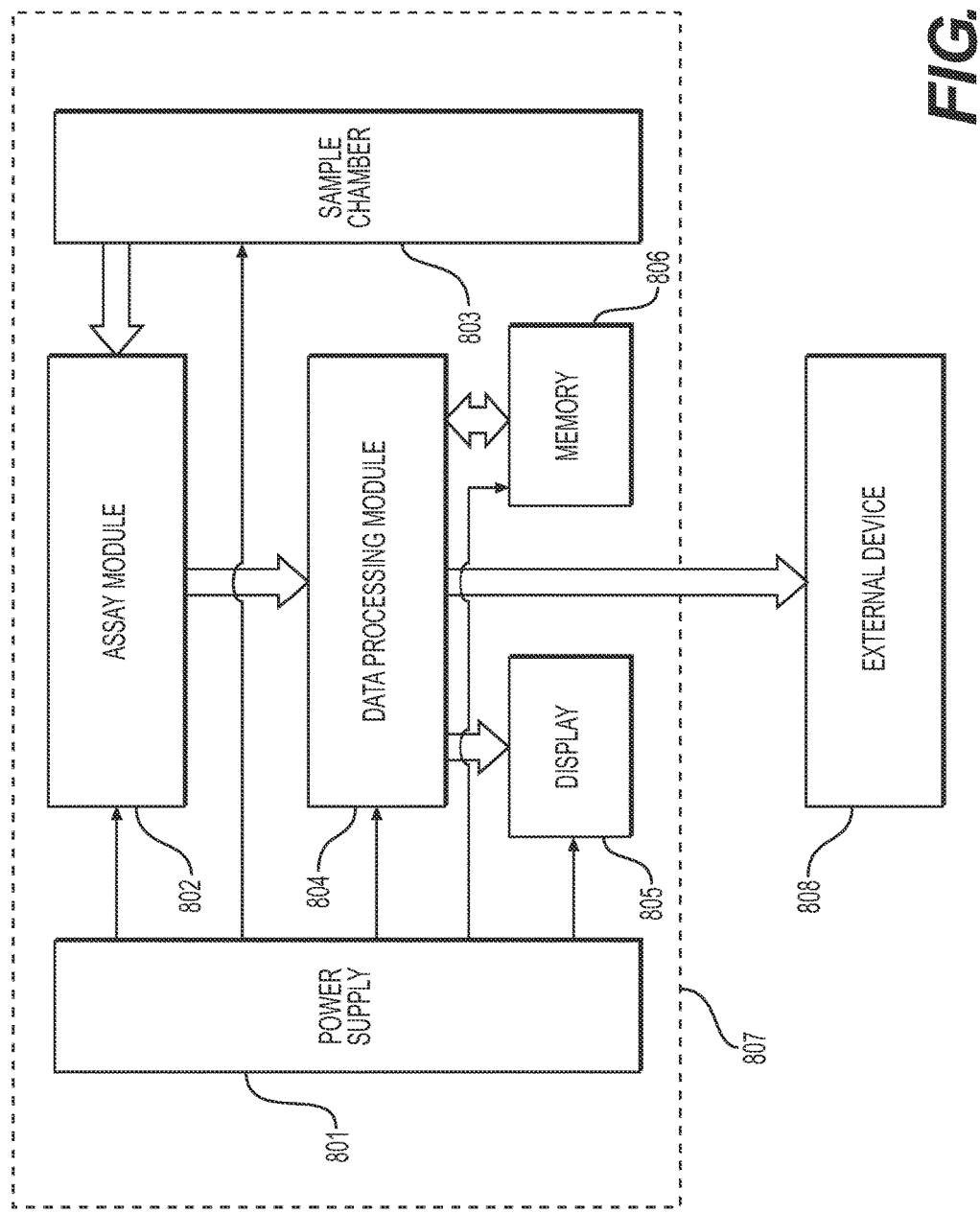
FIG. 8 is a schematic view of the in vitro diagnostic device.

FIG. 8 schematically illustrates the inventive in vitro diagnostic device. An inventive in vitro diagnostic device includes at least a sample collection chamber 803 and an assay module 802 used to detect biomarkers of psychiatric disorders. The in vitro diagnostic device may be a handheld device, a bench top device, or a point of care device.

The sample chamber 803 can be of any sample collection apparatus known in the art for holding a biological fluid. In one embodiment, the sample collection chamber can accommodate any one of the biological fluids herein contemplated, such as whole blood, plasma, serum, CSF, urine, saliva, sweat, buccal sample, prefrontal cortex tissue, hippocampus tissue, or ipsilateral cortex tissue.

The assay module 802 is preferably comprised of an assay which may be used for detecting RNA in a biological sample, for instance, through the use of probes and hybridization buffers in an immunoassay. In some embodiments the probes are labeled, such as radiolabeled. The assay module 802 may include of any assay currently known in the art; however the assay should be optimized for the detection of the micro RNA biomarkers used for detecting neural injuries, neuronal disorders or psychiatric disorders in a subject. The assay module 802 is in fluid communication with the sample collection chamber 803. In one embodiment, the assay module 802 is comprised of an immunoassay where the immunoassay may be any one of a radioimmunoassay, ELISA (enzyme linked immunosorbent assay), "sandwich" immunoassay, immunoprecipitation assay, precipitin reactions, gel diffusion precipitin reactions, immunodiffusion assay, fluorescent immunoassay, chemiluminescent immunoassay, phosphorescent immunoassay, or an anodic stripping voltammetry immunoassay. In one embodiment a colorimetric assay may be used which may comprise only of a sample collection chamber 803 and an assay module 802 of the assay. Although not specifically shown these components are preferably housed in one assembly 807. In one embodiment the assay module 802 contains agents specific for measuring miR-142-5p, miR-19b, miR-1928, miR-223-3p, miR-322*, miR-324, miR-421-3p, miR-463* and miR-674* or any combination, fragment or breakdown product thereof. In another embodiment the assay module 802 contains reagents specific for measuring miR-19b-3p, miR-223-3p and miR-221-3p or any combination, fragment or breakdown product thereof. Still, in other embodiments the assay module 802 contains agents specific for measuring at least one micro RNA of miR-142-5p, miR-19b, miR-1928, miR-223-3p, miR-322*, miR-324, miR-421-3p, miR-463* and miR-674* or any combination, fragment or breakdown product thereof. The assay module 802 may contain additional agents to detect additional biomarkers, as is described herein. Due to the co-morbidity of the PTSD with TBI, the inventive IVD may also measure the same biomarkers to correlate the presence or amount of the biomarkers with the presence and severity of TBI.

In another preferred embodiment, the inventive in vitro diagnostic device contains a power supply 801, an assay module 802, a sample chamber 803, and a data processing module 805. The power supply 801 is electrically connected to the assay module and the data processing module. The assay module 802 and the data processing module 805 are in electrical communication with each other. As described above, the assay module 802 may be comprised of any assay currently known in the art; however the assay should be optimized for the detection of neural biomarkers used for detecting neural injury, neuronal disorder or psychiatric disorders in a subject. The assay module 802 is in fluid communication with the sample collection chamber 803. The assay module 802 is comprised of an immunoassay where the immunoassay may be any one of a radioimmunoassay, ELISA (enzyme linked immunosorbent assay), "sandwich" immunoassay, immunoprecipitation assay, precipitin reactions, gel diffusion precipitin reactions, immunodiffusion assay, fluorescent immunoassay, chemiluminescent immunoassay, phosphorescent immunoassay, or an anodic stripping voltammetry immunoassay. A biological sample is placed in the sample chamber 803 and assayed by the assay module 802 detecting for a biomarker of psychiatric disorder. The measured amount of the biomarker by the assay module 802 is then electrically communicated to the data processing module 804. The data processing 804 module may comprise of any known data processing element known in the art, and may comprise of a chip, a central processing unit (CPU), or a software package which processes the information supplied from the assay module 802.

In one embodiment, the data processing module 804 is in electrical communication with a display 805, a memory device 806, or an external device 808 or software package (such as laboratory and information management software (LIMS)). In one embodiment, the data processing module 804 is used to process the data into a user defined usable format. This format comprises of the measured amount of neural biomarkers detected in the sample, indication that a neural injury, neuronal disorder, or psychiatric disorder is present, or indication of the severity of the neural injury, neuronal disorder or psychiatric disorder. The information from the data processing module 804 may be illustrated on the display 805, saved in machine readable format to a memory device, or electrically communicated to an external device 808 for additional processing or display. Although not specifically shown these components are preferably housed in one assembly 807. In one embodiment, the data processing module 804 may be programmed to compare the detected amount of the biomarker transmitted from the assay module 802, to a comparator algorithm. The comparator algorithm may compare the measure amount to the user defined threshold which may be any limit useful by the user. In one embodiment, the user defined threshold is set to the amount of the biomarker measured in control subject, or a statistically significant average of a control population.

The methods and in vitro diagnostic tests described herein may indicate diagnostic information to be included in the current diagnostic evaluation in patients suspected of having neural injury, neuronal disorder or psychiatric disorder. In another embodiment, the methods and in vitro diagnostic tests described herein may be used for screening for risk of progressing from at-risk, non-specific symptoms possibly associated with psychiatric disorders, and/or fully-diagnosed psychiatric disorders. In certain embodiments, the methods and in vitro diagnostic tests described herein can be used to rule out screening of diseases and disorders that share symptoms with psychiatric disorder.

In one embodiment, an in vitro diagnostic test may comprise one or more devices, tools, and equipment configured to hold or collect a biological sample from an individual. In one embodiment of an in vitro diagnostic test, tools to collect a biological sample may include one or more of a swab, a scalpel, a syringe, a scraper, a container, and other devices and reagents designed to facilitate the collection, storage, and transport of a biological sample. In one embodiment, an in vitro diagnostic test may include reagents or solutions for collecting, stabilizing, storing, and processing a biological sample. Such reagents and solutions for nucleotide collecting, stabilizing, storing, and processing are well known by those of skill in the art and may be indicated by specific methods used by an in vitro diagnostic test as described herein. In another embodiment, an in vitro diagnostic test as disclosed herein, may comprise a micro array apparatus and reagents, a flow cell apparatus and reagents, a multiplex nucleotide sequencer and reagents, and additional hardware and software necessary to assay a genetic sample for certain genetic markers and to detect and visualize certain biological markers.

Biomarkers

The present invention provides a process to detect micro RNAs, for the detection of psychiatric disorders, for example PTSD. These same micro RNAs may also be used to detect neural injuries and neuronal disorders, such as TBI, which is often comorbid with many psychiatric disorders. In one embodiment, at least one, more than one, or all micro RNAs specific to PTSD are detected and is selected from: miR-142-5p, miR-19b, miR-1928, miR-223-3p, miR-322*, miR-324, miR-421-3p, miR-463* and miR-674* or any combination, fragment or breakdown product thereof. In at least one embodiment that real-time polymerase chain reaction (PCR) measures the micro RNA level of the biomarker in a biological sample taken from a patient presenting with symptoms of PTSD or TBI and compared with levels of the micro RNA in samples from normal patients or historical levels of the patient. Without being bound to any particular theory, and without limiting the invention to these particular μRNAs, Table 1 provides at least one embodiment of exemplary micro RNA biomarkers as a result of their modulation after a PTSD inducing event is experienced by a subject, and detected fourteen (14) days after a trauma inducing event.

TABLE 1

| S# | TLDA ID | MicroRNA Symbol | MirBase ID | Mature Sequence | Serum Day 14 Fold change | Serum Day 14 P value | Amygdala Day 14 Fold change | Amygdala Day 14 P value |
|---|---|---|---|---|---|---|---|---|
| 1 | mmu-miR-142-5p-002248 | rno-miR-142-5p | MIMAT0000847 | cauaaaguagaaagcacuacu | 2.95 | 0.029 | 2.1 | 0.001 |
| 2 | mmu-miR-19b-000396 | rno-miR-19b-3p | MIMAT0000788 | ugugcaaauccaugcaaaacuga | 3.13 | 0.018 | 2.37 | 0 |
| 3 | mmu-miR-1928-121164_mat | rno-miR-221-3p | MIMAT0000890 | agcuacauugucugcugguuuc | 11.23 | 0.001 | 7.85 | 0 |
| 4 | mmu-miR-223-002295 | rno-miR-223-3p | MIMAT0000892 | ugucaguuugucaaauacccc | 4.25 | 0.001 | 2.16 | 0.033 |
| 5 | mmu-miR-322#-002506 | rno-miR-322-3p | MIMAT0000547 | aaacaugaagcgcugcaaca | 2.25 | 0.048 | 2 | 0.013 |
| 6 | mmu-miR-324-3p-002509 | rno-miR-324-3p | MIMAT0000554 | ccacugcccaggugcugcugg | 2.06 | 0.015 | 2.42 | 0.007 |

TABLE 1-continued

| | | | | | Serum Day 14 | | Amygdala Day 14 | |
|---|---|---|---|---|---|---|---|---|
| S# | TLDA ID | MicroRNA Symbol | MirBase ID | Mature Sequence | Fold change | P value | Fold change | P value |
| 7 | hsa-miR-421-002700 | rno-miR-421-3p | MIMAT0017175 | aucaacagacauuaauuggg | 3.96 | 0.001 | 2.1 | 0.009 |
| 8 | mmu-miR-463#-002582 | rno-miR-463-5p | MIMAT0017309 | uaccuaauuguuguccauca | 9.97 | 0.006 | 3.16 | 0.01 |
| 9 | mmu-miR-674#-001956 | rno-miR-674-3p | MIMAT0005330 | cacagcucccaucucagaacaa | 2.3 | 0.037 | 2.22 | 0.016 |

Other micro RNAs may alternatively be used. Table 2 provides PTSD potential biomarker micro RNA candidates experimentally validated targets from miRWalk database suitable for the diagnostics of PTSD or TBI.

TABLE 2

| S# | MicroRNA Name | StemLoop Name | miR_Chr | Gene Name | EntrezID | Pubmed ID |
|---|---|---|---|---|---|---|
| 1 | rno-miR-322* | rno-mir-322 | X | Egfr | 24329 | 17889671 |
| 2 | rno-miR-322* | rno-mir-322 | X | MBP_RAT | 24547 | 20215419 |
| 3 | rno-miR-223 | rno-mir-223 | X | Stx1a | 116470 | 18258830 |
| 4 | rno-miR-223 | rno-mir-223 | X | Akt1 | 24185 | 19074548 |
| 5 | rno-miR-223 | rno-mir-223 | X | Igf1r | 25718 | 22425712 |
| 6 | rno-miR-223 | rno-mir-223 | X | Blr1 | 29363 | 22984081 |
| 7 | rno-miR-223 | rno-mir-223 | X | Fgf16 | 60464 | 18258830 |
| 8 | rno-miR-223 | rno-mir-223 | X | Mmp9 | 81687 | 18258830 |
| 9 | rno-miR-223 | rno-mir-223 | X | NOTC1_RAT | 25496 | 20826802 |
| 10 | rno-miR-223 | rno-mir-223 | X | Adora1 | 29290 | 18258830 |
| 11 | rno-miR-223 | rno-mir-223 | X | Scn3a | 497770 | 18258830 |
| 12 | rno-miR-223 | rno-mir-223 | X | Itch | 311567 | 19074548 |
| 13 | rno-miR-223 | rno-mir-223 | X | Frap1 | 56718 | 22425712 |
| 14 | rno-miR-223 | rno-mir-223 | X | Cd4 | 24932 | 23153510 |
| 15 | rno-miR-223 | rno-mir-223 | X | Capn8 | 170808 | 18258830 |
| 16 | rno-miR-223 | rno-mir-223 | X | Kcnj16 | 29719 | 18258830 |
| 17 | rno-miR-223 | rno-mir-223 | X | Kitl | 60427 | 20826802 |
| 18 | rno-miR-223 | rno-mir-223 | X | CPG2 | 499010 | 18258830 |
| 19 | rno-miR-223 | rno-mir-223 | X | Gad1 | 24379 | 18258830 |
| 20 | rno-miR-223 | rno-mir-223 | X | Zap70 | 301348 | 19144983 |
| 21 | rno-miR-223 | rno-mir-223 | X | Cd4 | 24932 | 22527633 |
| 22 | rno-miR-223 | rno-mir-223 | X | Bcl2 | 24224 | 23208072 |
| 23 | rno-miR-223 | rno-mir-223 | X | Dhcr24 | 298298 | 18258830 |
| 24 | rno-miR-223 | rno-mir-223 | X | Runx1 | 50662 | 18416028 |
| 25 | rno-miR-223 | rno-mir-223 | X | Frap1 | 56718 | 20826802 |
| 26 | rno-miR-223 | rno-mir-223 | X | Ptges | 59103 | 18258830 |
| 27 | rno-miR-223 | rno-mir-223 | X | Fgfr1 | 79114 | 18258830 |
| 28 | rno-miR-223 | rno-mir-223 | X | Lmo2 | 362176 | 19278969 |
| 29 | rno-miR-223 | rno-mir-223 | X | Tnf | 24835 | 22562984 |
| 30 | rno-miR-223 | rno-mir-223 | X | Tra1_predicted | 362862 | 23208072 |
| 31 | rno-miR-223 | rno-mir-223 | X | Madd | 94193 | 18258830 |
| 32 | rno-miR-223 | rno-mir-223 | X | Stmn1 | 29332 | 18555017 |
| 33 | rno-miR-223 | rno-mir-223 | X | Zap70 | 301348 | 20862275 |
| 34 | rno-miR-223 | rno-mir-223 | X | Vsnl1 | 24877 | 18258830 |
| 35 | rno-miR-223 | rno-mir-223 | X | Il6 | 24498 | 22959936 |
| 36 | rno-miR-223 | rno-mir-223 | X | Dclk1 | 83825 | 18258830 |
| 37 | rno-miR-223 | rno-mir-223 | X | Cd4 | 24932 | 19297609 |
| 38 | rno-miR-223 | rno-mir-223 | X | Akt1 | 24185 | 23208072 |
| 39 | rno-miR-223 | rno-mir-223 | X | Klf15 | 85497 | 18258830 |
| 40 | rno-miR-223 | rno-mir-223 | X | Ifng | 25712 | 18791161 |
| 41 | rno-miR-223 | rno-mir-223 | X | NP_001102651.1 | 499593 | 21109969 |
| 42 | rno-miR-223 | rno-mir-223 | X | Golph3 | 78961 | 18258830 |
| 43 | rno-miR-223 | rno-mir-223 | X | Casp4 | 114555 | 22959936 |
| 44 | rno-miR-223 | rno-mir-223 | X | Neurod1 | 29458 | 18258830 |
| 45 | rno-miR-223 | rno-mir-223 | X | Frap1 | 56718 | 23208072 |
| 46 | rno-miR-223 | rno-mir-223 | X | Slc17a7 | 116638 | 18258830 |
| 47 | rno-miR-223 | rno-mir-223 | X | Rhob | 64373 | 19850724 |
| 48 | rno-miR-223 | rno-mir-223 | X | Bcl2 | 24224 | 17260024 |
| 49 | rno-miR-223 | rno-mir-223 | X | Nos2 | 24599 | 18791161 |
| 50 | rno-miR-223 | rno-mir-223 | X | NP_001099865.1 | 294515 | 21926415 |
| 51 | rno-miR-223 | rno-mir-223 | X | Nol3 | 85383 | 18258830 |
| 52 | rno-miR-223 | rno-mir-223 | X | LOC685953 | 29184 | 22959936 |
| 53 | rno-miR-223 | rno-mir-223 | X | Itgb1 | 24511 | 18258830 |

TABLE 2-continued

| S# | MicroRNA Name | StemLoop Name | miR_Chr | Gene Name | EntrezID | Pubmed ID |
|---|---|---|---|---|---|---|
| 54 | rno-miR-223 | rno-mir-223 | X | Mgst1 | 171341 | 18258830 |
| 55 | rno-miR-223 | rno-mir-223 | X | Sars1 | 266975 | 19915717 |
| 56 | rno-miR-223 | rno-mir-223 | X | Runx1 | 50662 | 17996649 |
| 57 | rno-miR-223 | rno-mir-223 | X | Hyou1 | 192235 | 18258830 |
| 58 | rno-miR-223 | rno-mir-223 | X | Cd4 | 24932 | 19014482 |
| 59 | rno-miR-223 | rno-mir-223 | X | Smad7 | 81516 | 21940491 |
| 60 | rno-miR-223 | rno-mir-223 | X | Il10 | 25325 | 22959936 |
| 61 | rno-miR-223 | rno-mir-223 | X | Vim | 81818 | 18258830 |
| 62 | rno-miR-223 | rno-mir-223 | X | Gpd1 | 60666 | 18258830 |
| 63 | rno-miR-223 | rno-mir-223 | X | Cd4 | 24932 | 19931339 |
| 64 | rno-miR-223 | rno-mir-223 | X | Aqp4 | 25293 | 18258830 |
| 65 | rno-miR-223 | rno-mir-223 | X | Akap6 | 64553 | 18258830 |
| 66 | rno-miR-223 | rno-mir-223 | X | Lmo2 | 362176 | 19017354 |
| 67 | rno-miR-223 | rno-mir-223 | X | Clec4d | 362432 | 22145958 |
| 68 | rno-miR-223 | rno-mir-223 | X | Tnf | 24835 | 22959936 |
| 69 | rno-miR-223 | rno-mir-223 | X | Ogt | 26295 | 18258830 |
| 70 | rno-miR-223 | rno-mir-223 | X | Gnb1 | 24400 | 18258830 |
| 71 | rno-miR-223 | rno-mir-223 | X | Slc2a4 | 25139 | 20080987 |
| 72 | rno-miR-223 | rno-mir-223 | X | Syt4 | 64440 | 18258830 |
| 73 | rno-miR-223 | rno-mir-223 | X | Tagln | 25123 | 18258830 |
| 74 | rno-miR-223 | rno-mir-223 | X | Lmo2 | 362176 | 19047678 |
| 75 | rno-miR-223 | rno-mir-223 | X | NOTC1_RAT | 25496 | 22424712 |
| 76 | rno-miR-223 | rno-mir-223 | X | Fos | 314322 | 22959936 |
| 77 | rno-miR-223 | rno-mir-223 | X | Tpm1_v7 | 24851 | 18258830 |
| 78 | rno-miR-223 | rno-mir-223 | X | Mapre1 | 114764 | 18258830 |
| 79 | rno-miR-223 | rno-mir-223 | X | Cd4 | 24932 | 20448109 |
| 80 | rno-miR-223 | rno-mir-223 | X | Hmox1 | 24451 | 18258830 |
| 81 | rno-miR-223 | rno-mir-223 | X | Acvr1 | 79558 | 18258830 |
| 82 | rno-miR-223 | rno-mir-223 | X | Itgam | 25021 | 19059913 |
| 83 | rno-miR-223 | rno-mir-223 | X | Igf1r | 25718 | 22424712 |
| 84 | rno-miR-223 | rno-mir-223 | X | Scd2 | 83792 | 22959936 |
| 85 | rno-miR-223 | rno-mir-223 | X | Mapk1 | 116590 | 18258830 |
| 86 | rno-miR-223 | rno-mir-223 | X | Nr4a1 | 79240 | 18258830 |
| 87 | rno-miR-223 | rno-mir-223 | X | NP_001102651.1 | 499593 | 20676373 |
| 88 | rno-miR-223 | rno-mir-223 | X | Gmfb | 81661 | 18258830 |
| 89 | rno-miR-221 | rno-mir-221 | X | Zbtb16 | 353227 | 18417445 |
| 90 | rno-miR-221 | rno-mir-221 | X | Zfhx1b | 311071 | 20516212 |
| 91 | rno-miR-221 | rno-mir-221 | X | Cdkn1b | 83571 | 19767219 |
| 92 | rno-miR-221 | rno-mir-221 | X | Met | 24553 | 21537871 |
| 93 | rno-miR-221 | rno-mir-221 | X | Cdkn1b | 83571 | 19150885 |
| 94 | rno-miR-221 | rno-mir-221 | X | NP_001028929.1 | 246060 | 20975375 |
| 95 | rno-miR-221 | rno-mir-221 | X | Pten | 50557 | 20021821 |
| 96 | rno-miR-221 | rno-mir-221 | X | Icam1 | 25464 | 22535415 |
| 97 | rno-miR-221 | rno-mir-221 | X | BIM_RAT | 64547 | 19438724 |
| 98 | rno-miR-221 | rno-mir-221 | X | Agt | 24179 | 21310411 |
| 99 | rno-miR-221 | rno-mir-221 | X | Mycn | 298894 | 17943719 |
| 100 | rno-miR-221 | rno-mir-221 | X | Cdkn1b | 83571 | 20428775 |
| 101 | rno-miR-221 | rno-mir-221 | X | Cdkn1b | 83571 | 18417445 |
| 102 | rno-miR-221 | rno-mir-221 | X | Cdkn1b | 83571 | 20547861 |
| 103 | rno-miR-221 | rno-mir-221 | X | Cdkn1b | 83571 | 19859555 |
| 104 | rno-miR-221 | rno-mir-221 | X | Cd4 | 24932 | 21788445 |
| 105 | rno-miR-221 | rno-mir-221 | X | NP_001028929.1 | 246060 | 19150885 |
| 106 | rno-miR-221 | rno-mir-221 | X | NP_001102171.1 | 362686 | 21076613 |
| 107 | rno-miR-221 | rno-mir-221 | X | Kras | 24525 | 20093556 |
| 108 | rno-miR-221 | rno-mir-221 | X | Tnf | 24835 | 22562984 |
| 109 | rno-miR-221 | rno-mir-221 | X | Mapk3 | 50689 | 19438724 |
| 110 | rno-miR-221 | rno-mir-221 | X | Vcam1 | 25361 | 21310411 |
| 111 | rno-miR-221 | rno-mir-221 | X | Myc | 24577 | 17943719 |
| 112 | rno-miR-221 | rno-mir-221 | X | NP_001028929.1 | 246060 | 20428775 |
| 113 | rno-miR-221 | rno-mir-221 | X | Stmn1 | 29332 | 18555017 |
| 114 | rno-miR-221 | rno-mir-221 | X | Cdkn1b | 83571 | 20618998 |
| 115 | rno-miR-221 | rno-mir-221 | X | Dbi | 25045 | 19953484 |
| 116 | rno-miR-221 | rno-mir-221 | X | Adam17 | 57027 | 22009755 |
| 117 | rno-miR-221 | rno-mir-221 | X | Cdkn1a | 114851 | 19153141 |
| 118 | rno-miR-221 | rno-mir-221 | X | Runx1 | 50662 | 21076613 |
| 119 | rno-miR-221 | rno-mir-221 | X | Map2k1 | 170851 | 20299489 |
| 120 | rno-miR-221 | rno-mir-221 | X | Cdkn1b | 83571 | 22992757 |
| 121 | rno-miR-221 | rno-mir-221 | X | Cdkn1b | 83571 | 19615744 |
| 122 | rno-miR-221 | rno-mir-221 | X | Socs1 | 252971 | 21355095 |
| 123 | rno-miR-221 | rno-mir-221 | X | Dnd1 | 307492 | 18155131 |
| 124 | rno-miR-221 | rno-mir-221 | X | Ttpa | 25571 | 20435889 |
| 125 | rno-miR-221 | rno-mir-221 | X | Cxcr4 | 60628 | 18647411 |
| 126 | rno-miR-221 | rno-mir-221 | X | NP_001028929.1 | 246060 | 20618998 |
| 127 | rno-miR-221 | rno-mir-221 | X | Cdkn1b | 83571 | 19953484 |
| 128 | rno-miR-221 | rno-mir-221 | X | Akt1 | 24185 | 22009755 |
| 129 | rno-miR-221 | rno-mir-221 | X | Cdkn1b | 83571 | 19153141 |
| 130 | rno-miR-221 | rno-mir-221 | X | Cdkn1b | 83571 | 21109963 |

TABLE 2-continued

| S# | MicroRNA Name | StemLoop Name | miR_Chr | Gene Name | EntrezID | Pubmed ID |
|---|---|---|---|---|---|---|
| 131 | rno-miR-221 | rno-mir-221 | X | Fos | 314322 | 20299489 |
| 132 | rno-miR-221 | rno-mir-221 | X | Met | 24553 | 23380809 |
| 133 | rno-miR-221 | rno-mir-221 | X | Bmf | 246142 | 19671867 |
| 134 | rno-miR-221 | rno-mir-221 | X | Cdkn1b | 83571 | 21355095 |
| 135 | rno-miR-221 | rno-mir-221 | X | Tnf | 24835 | 18246122 |
| 136 | rno-miR-221 | rno-mir-221 | X | Hnrpd | 79256 | 20435889 |
| 137 | rno-miR-221 | rno-mir-221 | X | Ephb1 | 24338 | 18704095 |
| 138 | rno-miR-221 | rno-mir-221 | X | Pten | 50557 | 20618998 |
| 139 | rno-miR-221 | rno-mir-221 | X | Amacr | 25284 | 20014922 |
| 140 | rno-miR-221 | rno-mir-221 | X | Nos3 | 24600 | 22037549 |
| 141 | rno-miR-221 | rno-mir-221 | X | Kras | 24525 | 19153141 |
| 142 | rno-miR-221 | rno-mir-221 | X | Adm | 25026 | 21122348 |
| 143 | rno-miR-221 | rno-mir-221 | X | Ephb1 | 24338 | 20299489 |
| 144 | rno-miR-221 | rno-mir-221 | X | Axin2 | 29134 | 23380809 |
| 145 | rno-miR-221 | rno-mir-221 | X | Cdkn1b | 83571 | 19671867 |
| 146 | rno-miR-221 | rno-mir-221 | X | Bcl2 | 24224 | 21400558 |
| 147 | rno-miR-221 | rno-mir-221 | X | Tnfsf10 | 246775 | 18246122 |
| 148 | rno-miR-221 | rno-mir-221 | X | Tnf | 24835 | 20435889 |
| 149 | rno-miR-221 | rno-mir-221 | X | Pten | 50557 | 18704095 |
| 150 | rno-miR-221 | rno-mir-221 | X | Cdkn1b | 83571 | 20818387 |
| 151 | rno-miR-221 | rno-mir-221 | X | Ddit4 | 140942 | 20018759 |
| 152 | rno-miR-221 | rno-mir-221 | X | Cdkn2a_v1 | 25163 | 22037549 |
| 153 | rno-miR-221 | rno-mir-221 | X | NP_001028929.1 | 246060 | 19153141 |
| 154 | rno-miR-221 | rno-mir-221 | X | Cdkn1b | 83571 | 21226887 |
| 155 | rno-miR-221 | rno-mir-221 | X | Tpm1_v7 | 24851 | 20417062 |
| 156 | rno-miR-221 | rno-mir-221 | X | NP_001028929.1 | 246060 | 19671867 |
| 157 | rno-miR-221 | rno-mir-221 | X | Tp53 | 24842 | 21400558 |
| 158 | rno-miR-221 | rno-mir-221 | X | Cdkn1b | 83571 | 18246122 |
| 159 | rno-miR-221 | rno-mir-221 | X | Bcl2 | 24224 | 20460378 |
| 160 | rno-miR-221 | rno-mir-221 | X | Cdkn1b | 83571 | 18708351 |
| 161 | rno-miR-221 | rno-mir-221 | X | Pdc | 25343 | 20822813 |
| 162 | rno-miR-221 | rno-mir-221 | X | Cdkn1b | 83571 | 20018759 |
| 163 | rno-miR-221 | rno-mir-221 | X | Mmp14 | 81707 | 22213426 |
| 164 | rno-miR-221 | rno-mir-221 | X | Cdkn1b | 83571 | 19264608 |
| 165 | rno-miR-221 | rno-mir-221 | X | NP_001028929.1 | 246060 | 21226887 |
| 166 | rno-miR-221 | rno-mir-221 | X | LOC685953 | 29184 | 17379065 |
| 167 | rno-miR-221 | rno-mir-221 | X | Rtn4 | 83765 | 20417062 |
| 168 | rno-miR-221 | rno-mir-221 | X | Cdkn1b | 83571 | 19730150 |
| 169 | rno-miR-221 | rno-mir-221 | X | Fas | 246097 | 21400558 |
| 170 | rno-miR-221 | rno-mir-221 | X | Bcl2 | 24224 | 18382364 |
| 171 | rno-miR-221 | rno-mir-221 | X | Stat5a | 24918 | 20489169 |
| 172 | rno-miR-221 | rno-mir-221 | X | Cdkn1b | 83571 | 19088079 |
| 173 | rno-miR-221 | rno-mir-221 | X | Cd4 | 24932 | 20822813 |
| 174 | rno-miR-221 | rno-mir-221 | X | Frap1 | 56718 | 20018759 |
| 175 | rno-miR-221 | rno-mir-221 | X | Cdkn2a_v1 | 25163 | 22213426 |
| 176 | rno-miR-221 | rno-mir-221 | X | Cdkn1b | 83571 | 19351832 |
| 177 | rno-miR-221 | rno-mir-221 | X | Cdkn1b | 83571 | 21273047 |
| 178 | rno-miR-221 | rno-mir-221 | X | NP_001099207.1 | 89804 | 17379831 |
| 179 | rno-miR-221 | rno-mir-221 | X | Inppl1 | 65038 | 20417062 |
| 180 | rno-miR-221 | rno-mir-221 | X | NP_001099886.1 | 294790 | 20492666 |
| 181 | rno-miR-221 | rno-mir-221 | X | Pten | 50557 | 19730150 |
| 182 | rno-miR-221 | rno-mir-221 | X | Akt1 | 24185 | 21481725 |
| 183 | rno-miR-221 | rno-mir-221 | X | Tp53 | 24842 | 18382364 |
| 184 | rno-miR-221 | rno-mir-221 | X | Cdkn1b | 83571 | 19107213 |
| 185 | rno-miR-221 | rno-mir-221 | X | Cdkn1b | 83571 | 20822813 |
| 186 | rno-miR-221 | rno-mir-221 | X | Bcl2 | 24224 | 20021821 |
| 187 | rno-miR-221 | rno-mir-221 | X | Egfr | 24329 | 22213426 |
| 188 | rno-miR-221 | rno-mir-221 | X | Npepps | 50558 | 19351832 |
| 189 | rno-miR-221 | rno-mir-221 | X | NP_001028929.1 | 246060 | 21278784 |
| 190 | rno-miR-221 | rno-mir-221 | X | Cdkn1b | 83571 | 17569667 |
| 191 | rno-miR-221 | rno-mir-221 | X | NP_001028929.1 | 246060 | 20417062 |
| 192 | rno-miR-221 | rno-mir-221 | X | Cdkn1b | 83571 | 20492666 |
| 193 | rno-miR-221 | rno-mir-221 | X | Cdkn1b | 83571 | 19749093 |
| 194 | rno-miR-221 | rno-mir-221 | X | Pten | 50557 | 21481725 |
| 195 | rno-miR-221 | rno-mir-221 | X | Cdkn1b | 83571 | 18413744 |
| 196 | rno-miR-221 | rno-mir-221 | X | Fabp4 | 79451 | 19126397 |
| 197 | rno-miR-221 | rno-mir-221 | X | Cxcl12 | 24772 | 20975375 |
| 198 | rno-miR-221 | rno-mir-221 | X | Tp53 | 24842 | 20021821 |
| 199 | rno-miR-221 | rno-mir-221 | X | Cdkn1b | 83571 | 22473819 |
| 200 | rno-miR-221 | rno-mir-221 | X | Akt1 | 24185 | 19401561 |
| 201 | rno-miR-221 | rno-mir-221 | X | Kcnh8 | 246325 | 21310411 |
| 202 | rno-miR-221 | rno-mir-221 | X | Cdkn1b | 83571 | 17627278 |
| 203 | rno-miR-221 | rno-mir-221 | X | Pdcd4 | 64031 | 20417062 |
| 204 | rno-miR-221 | rno-mir-221 | X | NP_001028929.1 | 246060 | 18413744 |
| 205 | rno-miR-221 | rno-mir-221 | X | Pi3 | 408230 | 20505758 |
| 206 | rno-miR-221 | rno-mir-221 | X | Tnfsf10 | 246775 | 19767219 |
| 207 | rno-miR-221 | rno-mir-221 | X | Eno2 | 24334 | 21487968 |

TABLE 2-continued

| S# | MicroRNA Name | StemLoop Name | miR_Chr | Gene Name | EntrezID | Pubmed ID |
|---|---|---|---|---|---|---|
| 208 | rno-miR-221 | rno-mir-221 | X | Cdkn1b | 83571 | 19126397 |
| 209 | rno-miR-221 | rno-mir-221 | X | Cdkn1b | 83571 | 20975375 |
| 210 | rno-miR-221 | rno-mir-221 | X | Cdkn1b | 83571 | 20021821 |
| 211 | rno-miR-221 | rno-mir-221 | X | NP_001028929.1 | 246060 | 22473819 |
| 212 | rno-miR-221 | rno-mir-221 | X | Ephb1 | 24338 | 19438724 |
| 213 | rno-miR-221 | rno-mir-221 | X | Agtr1a | 24180 | 21310411 |
| 214 | rno-miR-221 | rno-mir-221 | X | Cdkn1b | 83571 | 17721077 |
| 215 | rno-miR-221 | rno-mir-221 | X | NP_001102171.1 | 362686 | 20425795 |
| 216 | rno-miR-19b | rno-mir-19b-1 | 15 | Scpep1 | 114861 | 21527938 |
| 217 | rno-miR-19b | rno-mir-19b-2 | X | Hoxa7 | 500126 | 22362744 |
| 218 | rno-miR-19b | rno-mir-19b-2 | X | Bace1 | 29392 | 18434550 |
| 219 | rno-miR-19b | rno-mir-19b-2 | X | Pten | 50557 | 20851997 |
| 220 | rno-miR-19b | rno-mir-19b-1 | 15 | Nr3c2 | 25672 | 19944075 |
| 221 | rno-miR-19b | rno-mir-19b-1 | 15 | Myc | 24577 | 21664042 |
| 222 | rno-miR-19b | rno-mir-19b-2 | X | BIM_RAT | 64547 | 22362744 |
| 223 | rno-miR-19b | rno-mir-19b-2 | X | Socs1 | 252971 | 18728182 |
| 224 | rno-miR-19b | rno-mir-19b-2 | X | Ctgf | 64032 | 21501375 |
| 225 | rno-miR-19b | rno-mir-19b-1 | 15 | Myc | 24577 | 20008931 |
| 226 | rno-miR-19b | rno-mir-19b-1 | 15 | BIM_RAT | 64547 | 21664042 |
| 227 | rno-miR-19b | rno-mir-19b-2 | X | Tp53 | 24842 | 18728182 |
| 228 | rno-miR-19b | rno-mir-19b-2 | X | Rhob | 64373 | 21527938 |
| 229 | rno-miR-19b | rno-mir-19b-1 | 15 | Cdkn1a | 114851 | 20089119 |
| 230 | rno-miR-19b | rno-mir-19b-1 | 15 | Aps | 114203 | 21794077 |
| 231 | rno-miR-19b | rno-mir-19b-2 | X | Stat3 | 25125 | 19713220 |
| 232 | rno-miR-19b | rno-mir-19b-2 | X | Scpep1 | 114861 | 21527938 |
| 233 | rno-miR-19b | rno-mir-19b-1 | 15 | Kras | 24525 | 20089119 |
| 234 | rno-miR-19b | rno-mir-19b-1 | 15 | Bcl2 | 24224 | 21883694 |
| 235 | rno-miR-19b | rno-mir-19b-2 | X | Nr3c2 | 25672 | 19944075 |
| 236 | rno-miR-19b | rno-mir-19b-2 | X | Myc | 24577 | 21664042 |
| 237 | rno-miR-19b | rno-mir-19b-1 | 15 | Fmr1 | 24948 | 20435064 |
| 238 | rno-miR-19b | rno-mir-19b-1 | 15 | BIM_RAT | 64547 | 21883694 |
| 239 | rno-miR-19b | rno-mir-19b-2 | X | Myc | 24577 | 20008931 |
| 240 | rno-miR-19b | rno-mir-19b-1 | 15 | NP_00100814.1 | 306825 | 17575136 |
| 241 | rno-miR-19b | rno-mir-19b-2 | X | BIM_RAT | 64547 | 21664042 |
| 242 | rno-miR-19b | rno-mir-19b-1 | 15 | Myc | 24577 | 20851997 |
| 243 | rno-miR-19b | rno-mir-19b-1 | 15 | Runx1 | 50662 | 22362744 |
| 244 | rno-miR-19b | rno-mir-19b-2 | X | Cdkn1a | 114851 | 20089119 |
| 245 | rno-miR-19b | rno-mir-19b-1 | 15 | Hipk3 | 83617 | 17575136 |
| 246 | rno-miR-19b | rno-mir-19b-2 | X | Aps | 114203 | 21794077 |
| 247 | rno-miR-19b | rno-mir-19b-1 | 15 | Kras | 24525 | 20851997 |
| 248 | rno-miR-19b | rno-mir-19b-1 | 15 | Hoxa7 | 500126 | 22362744 |
| 249 | rno-miR-19b | rno-mir-19b-2 | X | Kras | 24525 | 20089119 |
| 250 | rno-miR-19b | rno-mir-19b-1 | 15 | Bace1 | 29392 | 18434550 |
| 251 | rno-miR-19b | rno-mir-19b-2 | X | Bcl2 | 24224 | 21883694 |
| 252 | rno-miR-19b | rno-mir-19b-1 | 15 | Pten | 50557 | 20851997 |
| 253 | rno-miR-19b | rno-mir-19b-1 | 15 | BIM_RAT | 64547 | 22362744 |
| 254 | rno-miR-19b | rno-mir-19b-2 | X | Fmr1 | 24948 | 20435064 |
| 255 | rno-miR-19b | rno-mir-19b-1 | 15 | Socs1 | 252971 | 18728182 |
| 256 | rno-miR-19b | rno-mir-19b-2 | X | BIM_RAT | 64547 | 21883694 |
| 257 | rno-miR-19b | rno-mir-19b-1 | 15 | Ctgf | 64032 | 21501375 |
| 258 | rno-miR-19b | rno-mir-19b-2 | X | NP_001100814.1 | 306825 | 17575136 |
| 259 | rno-miR-19b | rno-mir-19b-2 | X | Myc | 24577 | 20851997 |
| 260 | rno-miR-19b | rno-mir-19b-1 | 15 | Tp53 | 24842 | 18728182 |
| 261 | rno-miR-19b | rno-mir-19b-2 | X | Runx1 | 50662 | 22362744 |
| 262 | rno-miR-19b | rno-mir-19b-1 | 15 | Rhob | 64373 | 21527938 |
| 263 | rno-miR-19b | rno-mir-19b-2 | X | Hipk3 | 83617 | 17575136 |
| 264 | rno-miR-19b | rno-mir-19b-2 | X | Kras | 24525 | 20851997 |
| 265 | rno-miR-19b | rno-mir-19b-1 | 15 | Stat3 | 25125 | 19713220 |
| 266 | rno-miR-142-5p | rno-mir-142 | 10 | Ifng | 25712 | 21085987 |
| 267 | rno-miR-142-5p | rno-mir-142 | 10 | Nos2 | 24599 | 21085987 |
| 268 | rno-miR-142-5p | rno-mir-142 | 10 | Adarb1 | 25367 | 16369484 |
| 269 | rno-miR-142-5p | rno-mir-142 | 10 | Phb2 | 114766 | 21569818 |
| 270 | rno-miR-142-5p | rno-mir-142 | 10 | Scpep1 | 114861 | 16369484 |
| 271 | rno-miR-142-5p | rno-mir-142 | 10 | Ifit3 | 309526 | 22367717 |
| 272 | rno-miR-142-5p | rno-mir-142 | 10 | Apcs | 29339 | 19794140 |
| 273 | rno-miR-142-5p | rno-mir-142 | 10 | Apcs | 29339 | 22549634 |
| 274 | rno-miR-142-5p | rno-mir-142 | 10 | Cxcl9 | 246759 | 20178649 |
| 275 | rno-miR-142-5p | rno-mir-142 | 10 | Cd4 | 24932 | 22549634 |
| 276 | rno-miR-142-5p | rno-mir-142 | 10 | Twist2 | 59327 | 20178649 |
| 277 | rno-miR-142-5p | rno-mir-142 | 10 | Elovl6 | 171402 | 20178649 |
| 278 | rno-miR-142-5p | rno-mir-142 | 10 | Ddit4l | 140582 | 20178649 |
| 279 | rno-miR-142-5p | rno-mir-142 | 10 | Fmr1 | 24948 | 20435064 |
| 280 | rno-miR-142-5p | rno-mir-142 | 10 | Tnf | 24835 | 21085987 |
| 281 | rno-miR-421 | rno-mir-421 | X | Pten | 50557 | 19175831 |
| 282 | rno-miR-421 | rno-mir-421 | X | Mycn | 298894 | 20080624 |
| 283 | rno-miR-421 | rno-mir-421 | X | Smad4 | 50554 | 21352803 |
| 284 | rno-miR-421 | rno-mir-421 | X | Nr1h4 | 60351 | 22146319 |

TABLE 2-continued

| S# | MicroRNA Name | StemLoop Name | miR_Chr | Gene Name | EntrezID | Pubmed ID |
|---|---|---|---|---|---|---|
| 285 | mmu-miR-674 | mmu-mir-674 | 2 | Mbp | 17196 | 20215419 |
| 286 | mmu-miR-674 | mmu-mir-674 | 2 | Lin28 | 83557 | 20413612 |
| 287 | mmu-miR-463 | mmu-mir-463 | X | Tnp2 | 21959 | 15901636 |
| 288 | mmu-miR-463 | mmu-mir-463 | X | Mat1a | 11720 | 19507003 |
| 289 | mmu-miR-463 | mmu-mir-463 | X | Mbp | 17196 | 20215419 |
| 290 | mmu-miR-463 | mmu-mir-463 | X | Lin28 | 83557 | 20413612 |
| 291 | mmu-miR-324-3p | mmu-mir-324 | 11 | Ctdspl | 69274 | 17369397 |
| 292 | mmu-miR-324-3p | mmu-mir-324 | 11 | Hprt1 | 15452 | 17369397 |
| 293 | mmu-miR-324-3p | mmu-mir-324 | 11 | Oog4 | 242737 | 17369397 |
| 294 | mmu-miR-324-3p | mmu-mir-324 | 11 | Dnmt3b | 13436 | 17369397 |
| 295 | mmu-miR-324-3p | mmu-mir-324 | 11 | H2afx | 15270 | 17369397 |
| 296 | mmu-miR-324-3p | mmu-mir-324 | 11 | Fgf21 | 56636 | 17369397 |
| 297 | mmu-miR-324-3p | mmu-mir-324 | 11 | Mos | 17451 | 17369397 |
| 298 | mmu-miR-324-3p | mmu-mir-324 | 11 | Mtpn | 14489 | 15538371 |
| 299 | mmu-miR-324-3p | mmu-mir-324 | 11 | Mt1 | 17748 | 17369397 |
| 300 | mmu-miR-324-3p | mmu-mir-324 | 11 | Cdh1 | 12550 | 19559694 |
| 301 | mmu-miR-324-3p | mmu-mir-324 | 11 | Ccne1 | 12447 | 17369397 |
| 302 | mmu-miR-324-3p | mmu-mir-324 | 11 | Ccnb2 | 12442 | 17369397 |
| 303 | mmu-miR-324-3p | mmu-mir-324 | 11 | Stat3 | 20848 | 19559694 |
| 304 | mmu-miR-324-3p | mmu-mir-324 | 11 | Zp3 | 22788 | 17369397 |
| 305 | mmu-miR-324-3p | mmu-mir-324 | 11 | Rfpl4 | 192658 | 17369397 |
| 306 | mmu-miR-324-3p | mmu-mir-324 | 11 | Fgf10 | 14165 | 19559694 |
| 307 | mmu-miR-324-3p | mmu-mir-324 | 11 | Sycp3 | 20962 | 17369397 |
| 308 | mmu-miR-324-3p | mmu-mir-324 | 11 | H2afz | 51788 | 17369397 |
| 309 | mmu-miR-324-3p | mmu-mir-324 | 11 | Bmp4 | 12159 | 19559694 |
| 310 | mmu-miR-324-3p | mmu-mir-324 | 11 | Camk2g | 12325 | 17369397 |
| 311 | mmu-miR-324-3p | mmu-mir-324 | 11 | Dicer1 | 192119 | 17369397 |
| 312 | mmu-miR-324-3p | mmu-mir-324 | 11 | Mapk14 | 26416 | 19559694 |
| 313 | mmu-miR-324-3p | mmu-mir-324 | 11 | Pou5f1 | 18999 | 17369397 |
| 314 | mmu-miR-324-3p | mmu-mir-324 | 11 | H1foo | 171506 | 17369397 |
| 315 | mmu-miR-324-3p | mmu-mir-324 | 11 | Mbp | 17196 | 20215419 |
| 316 | mmu-miR-324-3p | mmu-mir-324 | 11 | Ifitm3 | 66141 | 17369397 |
| 317 | mmu-miR-324-3p | mmu-mir-324 | 11 | Dppa3 | 73708 | 17369397 |
| 318 | mmu-miR-324-3p | mmu-mir-324 | 11 | Lin28 | 83557 | 20413612 |
| 319 | mmu-miR-324-3p | mmu-mir-324 | 11 | Cpeb1 | 12877 | 17369397 |

In some embodiments of the inventive methods quantization of micro RNA is performed by Real-time RT-PCR. In at least one embodiment, about 1.5 µg total micro RNA is isolated from the biological samples of patients presenting with clinical symptoms of TBI and PTSD and reverse transcribed in a reaction volume of 20 µl using Taqman RT kit and micro RNA-specific primers. The product is diluted to a volume of 150 µl and 6 µl aliquots are used as templates for amplification using conventional PCR reagent kit components and gene-specific primers. In some embodiments, micro RNA can correlated with normal controls or historical controls with that of the corresponding micro RNA to detect modulation of the micro RNA in the injured patient, and based on the modulation of one or all of the micro RNAs a clinician can determine whether the patient is suffering from PTSD or TBI.

Kits

The process of measuring for micro RNA biomarkers or diagnosing PTSD or TBI may also be included as part of a kit for use in an ELISA, Northern Blot, Northern Analysis, hybridized buffers, probes, labeled probes or Western Blot, a bench top platform, a point of care device, or handheld device for diagnosing PTSD or other psychiatric disorders or TBI and other neural injuries. The PTSD and TBI biomarkers can also be used to screen for therapeutic targets for treating PTSD or TBI and to monitor a patient's progression or recovery from PTSD or TBI.

In certain embodiments, the diagnostic process and kits includes one or more agents for detecting one or more micro RNA biomarkers. The diagnostic process and kits also comprise two or more, three or more, four or more, five or more, six or more, seven or more, eight or more, nine or more, or ten or more agents or antibodies that bind to a protein identified as specific to a PTSD or TBI cluster to diagnose PTSD or TBI in a patient. The kits can support for the simultaneous measurement of a panel of micro RNA biomarkers, 3 micro RNA biomarkers, or at least one micro RNA biomarker.

An inventive kit is also provided for aiding a diagnosis of a PTSD or TBI wherein the kits can be used to detect any number of the diagnostic proteins of the present invention. For example, the kits can be used to detect whether the diagnostic protein markers are present in samples of a patient and normal subjects. An inventive kit is used to identify compounds that modulate expression of one or more of the markers using in vitro or in vivo animal models to determine the effects of treatment. An inventive kit includes (a) a composition or panel of biomarkers; (b) a substrate; and (c) a detection agent. Such kits are prepared from the materials described above, and the previous discussion regarding the materials (e.g., antibodies, detection reagents, immobilized supports, etc.) is fully applicable to this section and will not be repeated. Optionally, the kit includes prefractionation spin columns. In some embodiments, the kit optionally further includes instructions for reacting the agent with the biological sample, or other operation parameter to afford a diagnosis of the condition. The instructions, in the form of a label or a separate insert.

A kit is also provided that includes (a) a substrate with an adsorbent thereon, wherein the adsorbent is suitable for binding a marker, (b) any biomarker of the present invention to be tested, and (c) instructions to detect the marker or markers by contacting a sample with the adsorbent and detecting the marker or markers retained by the adsorbent.

In some embodiments, the kit includes an eluent (as an alternative or in combination with instructions) or instructions for making an eluent, wherein the combination of the adsorbent and the eluant allows detection of the markers using gas phase ion spectrometry. Such kits are prepared from the materials described above, and the previous discussion of these materials (e.g., probe substrates, adsorbents, washing solutions, etc.) is fully applicable to this section and is not repeated.

A kit is also provided that includes a first substrate with an adsorbent thereon such as a particle functionalized with an adsorbent and a second substrate onto which the first substrate is positioned to form a probe which is removable and insertable into a gas phase ion spectrometer. The kit optionally includes single substrate which is in the form of a removable and insertable probe with adsorbents on the substrate. The kit also optionally includes a prefractionation spin column (e.g., Cibacron blue agarose column, anti-HSA agarose column, size exclusion column, Q-anion exchange spin column, single stranded DNA column, lectin column, etc.).

Optionally, the kit also optionally includes instructions for suitable operational parameters in the form of a label or a separate insert. For example, the kit may have standard instructions informing a consumer how to wash the probe after a sample is contacted on the probe. In another example, the kit may have instructions for pre-fractionating a sample to reduce complexity of proteins in the sample. In another example, the kit may have instructions for automating the fractionation or other processes.

It should be appreciated that although serum and amygdala are illustrated in the following Examples the inventive biomarkers for PTSD and TBI may be detected identically using the same procedures identified, the only difference being how the biological sample is drawn, as the varying biological samples have different methods for collection as one having skill in the art should readily know.

EXAMPLES

Reference will now be made in detail to the exemplary embodiments of the invention. These embodiments are described in sufficient detail to enable those skilled in the art to practice the invention and it is to be understood that other embodiments may be utilized and that changes may be made without departing from the scope of the invention. The following description is, therefore, merely exemplary.

Example 1—Animals and Stress Protocol

Male albino Sprague Dawley rats (Taconic Farms, Germantown, N.Y., USA) weighing 76 to 100 g and aged between 4-6 weeks old were used. These animals were kept for acclimation for a week and then the rats were grouped into two groups of six animals each for stress and control. Young animals were used for this study to give sufficient time for simulating PTSD progression as seen in the battlefield scenario. Development of PTSD like symptoms take at least two weeks after the cessation of stressors in the animal model and hormonal changes occur immediately after stress exposure as compared to the molecular level changes (Servatius et al. 1995). Hence, young animals were used to give sufficient time for studying the molecular level changes like protein or gene expression during PTSD development. Housing conditions, acclimation of rats and the stress protocol were followed as previously described (Jia et al., 2012). The stress protocol consisted of a 2 h per day session of immobilization along with tail shocks for three consecutive days. These animals were restrained and exposed to 40 electric shocks (2 mA, 3 s duration) at varying intervals of 150-210 s. Control groups were handled similar to stress group such as acclimation and housing except for the stress protocol. The Institutional Animal Care and Use Committee of the USUHS approved all the experimental procedures. Not being bound by any particular theory it is understood that similar models can be used for TBI, and presentation of symptoms of TBI appear within 24 hours of the initial stress tests.

Example 2—RNA Isolation, Quantity and Quality Check

Total RNA including micro RNA was isolated from the serum samples using the miRNeasy Serum/Plasma Kit (Qiagen, Valencia, USA) according to the manufacturer's protocol. QIAzol lysis reagent (1 ml) was added to the serum sample (200 µL) and vortexed. After incubating at room temperature for 5 min, 200 µL of chloroform was added and the samples were incubated at room temperature for 2-3 min and centrifuged for 15 min at 12,000×g at 4° C. The aqueous phase obtained after centrifugation was mixed with 1.5 volume of 100% ethanol and loaded into an RNeasy MiniElute spin column in a 2 ml collection tube. The flow through after centrifugation was discarded and the column was washed with 700 µL of Buffer RWT, 500 µL of Buffer RPE, 500 µL of 80% ethanol and then finally eluted with 14 µL of RNase-free water.

Figure 5:
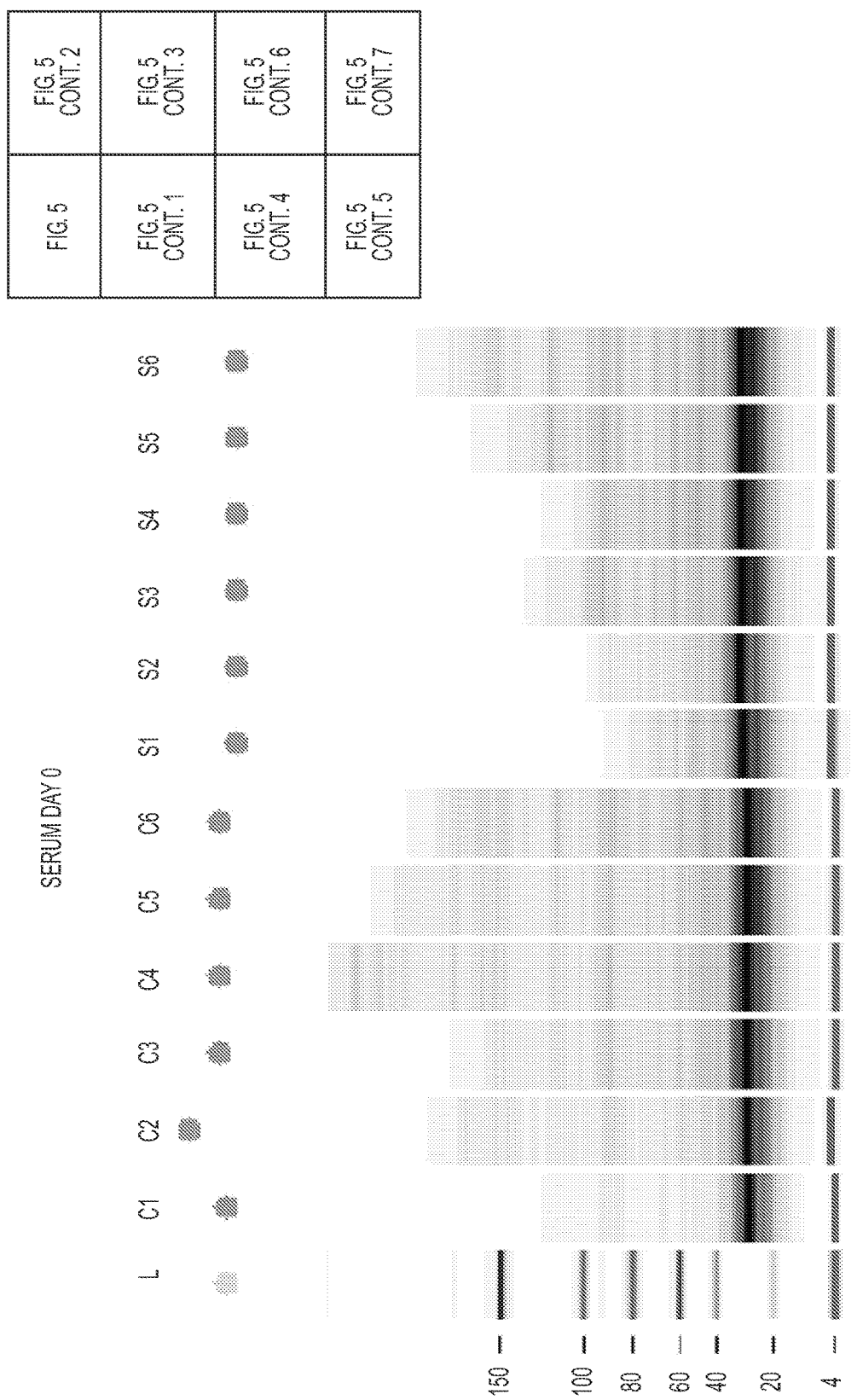
FIG. 5 shows electronic gel and electropherogram images of small RNA quality checking before performing micro RNA expression experiments from the serum and amygdala samples of control and posttraumatic stress.
Figure 5:
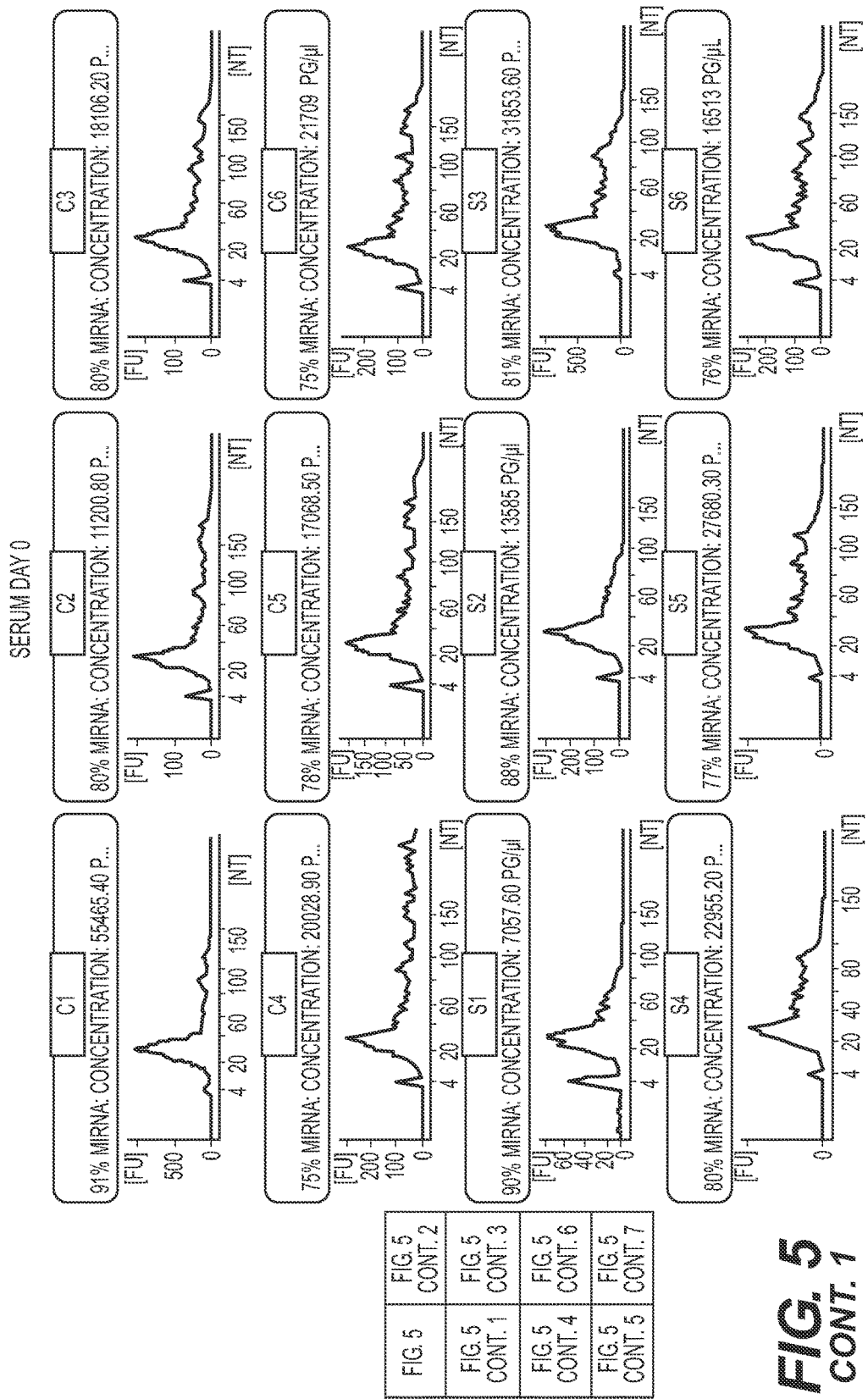
Figure 5:
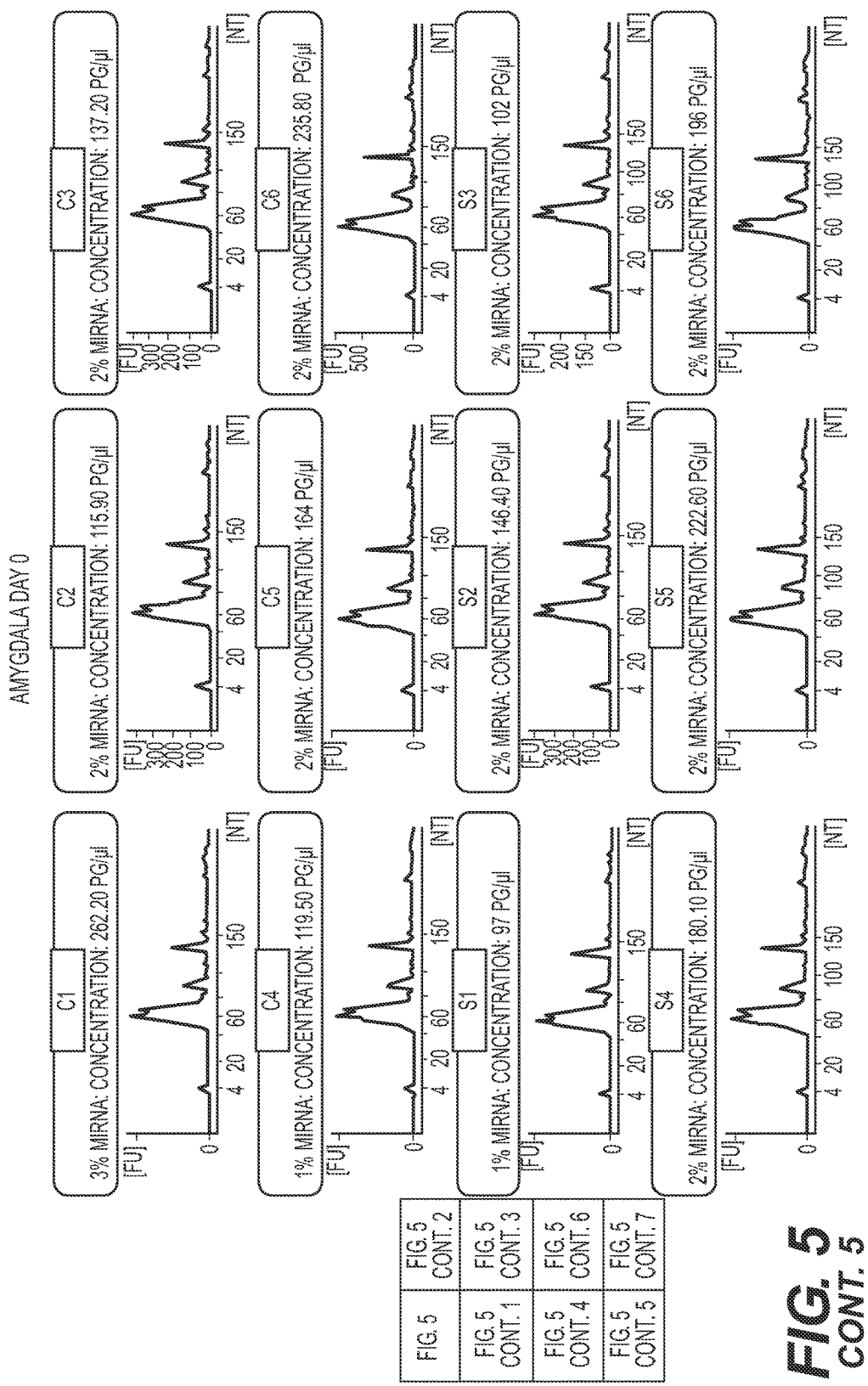
Figure 5:
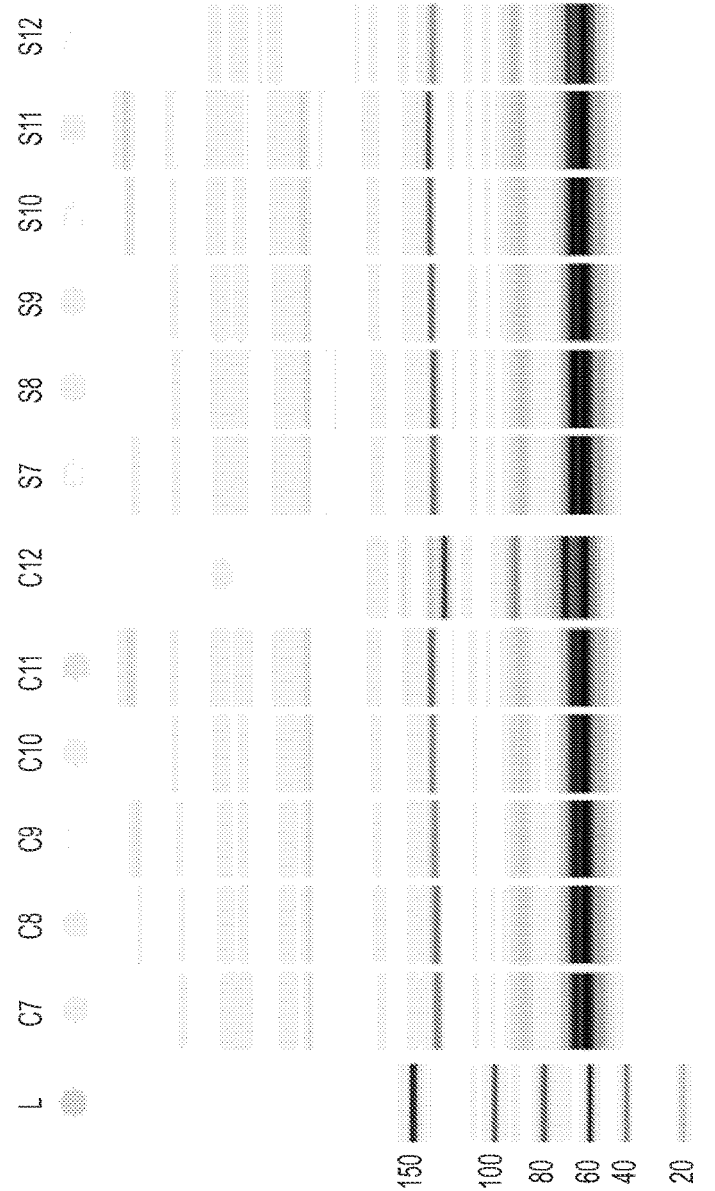
Figure 5:
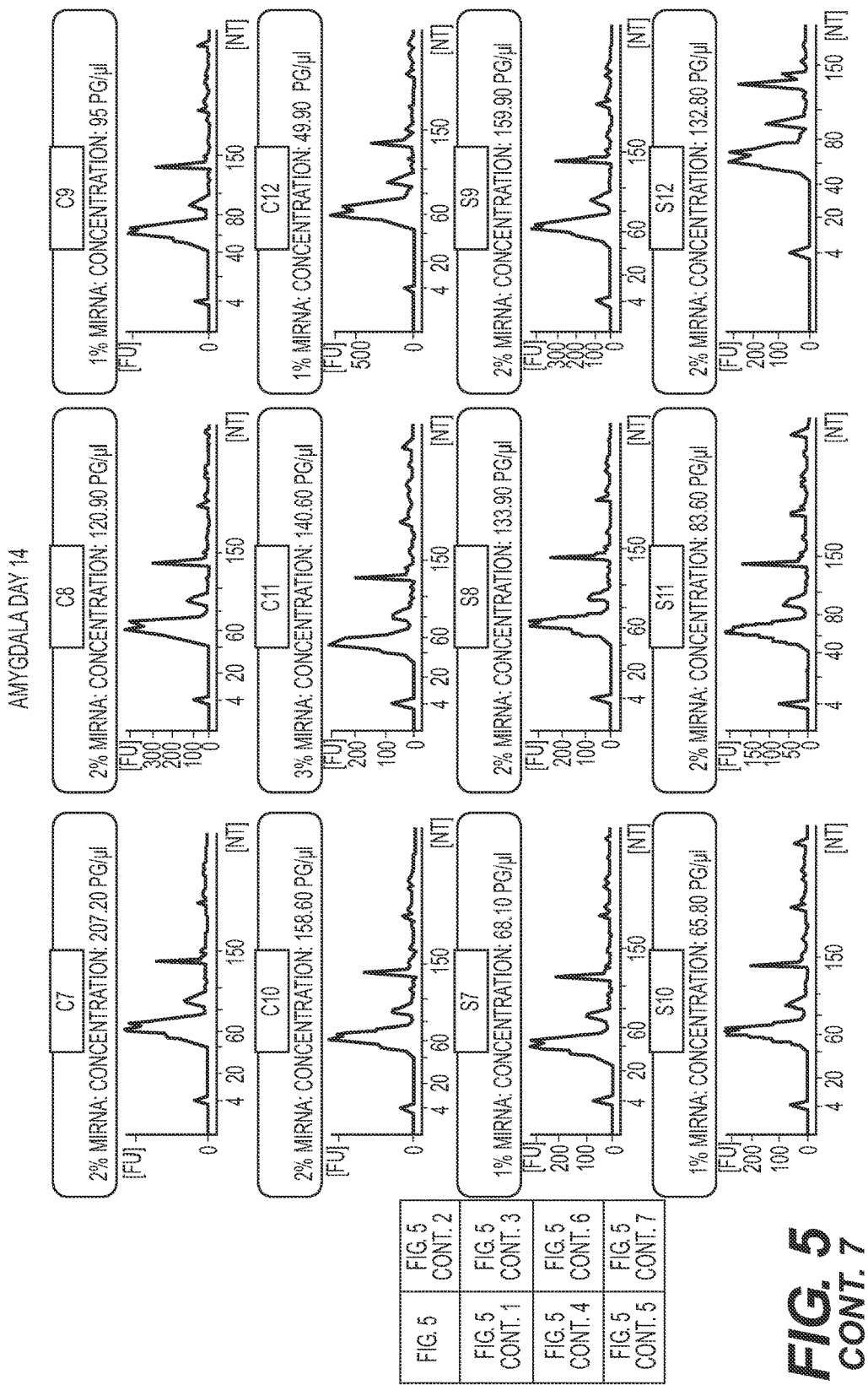

Total RNA was isolated from the amygdala tissue by combining a protocol of TRIzol reagent (Ambion/Life Technologies, Carlsbad, Calif., USA) and the mirVana µRNA isolation kit (Ambion/Life Technologies, Carlsbad, Calif., USA) according to the manufacturer's protocol. Briefly, two volumes of Trizol were added to the samples along with 1 volume of chloroform. After centrifugation, the aqueous layer was collected and mixed with 1.25 volume of absolute ethanol and passed through the RNAqueous micro kit cartridge and RNA eluted in TE buffer. Quality and quantity of small RNA for both serum and amygdala samples were analyzed using Agilent Small RNA kit (Agilent Technologies, Santa Clara, Calif., USA) in Agilent 2100 Bioanalyzer. Bioanalyzer data indicated the presence of good quality micro RNA in total serum RNA extractions. However, the micro RNA quantity in serum was an average of 15 ng/µl (FIG. 5). This was expected since micro RNAs have been reported to be present in serum at low concentration and most of them are secreted out of the cells (Sayed et al., 2013). micro RNA concentrations of 30 ng of serum and 5 ng of amygdala µRNAs were used for the PCR reactions.

Example 3—Reverse Transcription, Pre-Amplification and Real Time Quantitative PCR Reverse transcription (RT) was performed with TaqMan micro RNA RT Kit (Life Technologies, Carlsbad, Calif., USA) as described with slight modifications (Balakathiresan et al., 2012). micro RNA quantity was measured from the total RNA of bioanalyzer data and was used as template RNA (5 ng-brain µRNA; 30 ng-serum µRNA) for RT reactions (FIG. 5). Briefly, the RT reaction mixture contained 0.8 µl Megaplex RT primers Rodent Pool A/B (v3.0), 0.2 µl 100 mM dNTPs (with dTTP), 1.5 µl Multiscribe reverse transcriptase (50 U/µl), 0.8 µl 10×RT Buffer, 0.9 µl MgCl$_2$ (25 mM), 0.1 µl RNAse inhibitor (20 U/µl), RNA template and nuclease free water to a final volume of 7.5 µl.

RT reaction was carried out on Veriti 96-Well Thermal Cycler (Life Technologies, Carlsbad, Calif., USA) according to manufacturer's recommended thermal cycling conditions. Pre-amplification of RT products, cycles and conditions were followed according to the manufacturer's protocol (Life Technologies, Carlsbad, Calif., USA). The undiluted pre-amplification products were used for the micro RNA profiling using TaqMan Low Density Rodent microRNAs Array (TLDA) Set v3.0 (Applied Biosystems, Inc) containing 692 rodent micro RNAs. The quantitative PCR (qPCR) reaction was carried out at default thermal-cycling conditions in ABI 7900HT Fast Real-Time PCR System (Applied Biosystems, Life Technologies, Foster City, Calif.).

Example 4—TaqMan Micro RNA Assay

TaqMan micro RNA assays (Applied Biosystems, Life Technologies, Foster City, Calif.) were carried out to validate the changes in the expression of selected micro RNAs in serum and amygdala. RT was performed as per manufacturer's protocol using micro RNA specific RT primers and mammalian U6 small nuclear RNA (U6 snRNA) was used as an endogenous control for the validation of all selected micro RNAs. RT and RT-qPCR reactions were carried out as described in Balakathiresan et al (2012). TaqMan micro RNA assays were carried out in triplicate. For relative quantification, each micro RNA was calibrated to the expression of U6 snRNA, which then gave a delta CT ($\Delta$Ct) value for each μRNA (μRNA Ct value-U6 Ct value). The fold changes were calculated using the comparative Ct method ($2^{-\Delta\Delta Ct}$).

Micro RNA expression profiles for Ct values were analyzed using real-time StatMiner software (Integromics Inc) to identify significantly modulated stress-responsive micro RNAs. For relative quantification of μRNAs between control and traumatic stress exposed animals, the following steps were performed in the StatMiner software suite: quality control of biological replicates, selection of U6 snRNA as an optimal endogenous control, filtering of micro RNAs expression having Ct values below 35 cycles and the detection of expression in all biological replicates of calibrator and target. Statistically significant micro RNAs were selected based on p-value lower than 0.05.

Predicted targets of differentially expressed serum and amygdala micro RNAs downloaded from miRWalk, a target prediction algorithm, were analyzed. MiRWalk is a combinatorial μRNA-target prediction tool and is able to identify both predicted and validated targets (Dweep et al., 2011). Both functional and network analysis of altered micro RNA and their gene targets associated with fear responses were performed using Ingenuity Pathway Analysis (IPA) program (Ingenuity Systems Inc, Redwood City, Calif.).

Example 5—Analysis of RNA Signatures in Serum and Correlation with Amygdala

The micro RNA expression profiling identified 82 micro RNAs, which were differentially expressed at day 14 after traumatic stress, whereas only 18 micro RNAs were modulated in serum at day 0 after the cessation of stress. Thus micro RNA candidates in serum to diagnose PTSD are hereby presented. micro RNA expression in amygdala due to its critical role in fear conditioning (Morey et al., 2012) was also established. A comparison of micro RNAs expression profile in amygdala at day 0 and day 14 with serum μRNAs indicated a similar μRNA modulation pattern (Table 3).

TABLE 3

| | | Amygdala Day 0 | | Amygdala Day 14 | | |
|---|---|---|---|---|---|---|
| S# | Detector | RQ_Stress-Control | P. Value Stress-Control | Detector | RQ_Stress-Control | P. Value Stress-Control |
| 1 | mmu-miR-429 | 2.02 | 0.01 | rno-miR-632 | 742.43 | 0.01 |
| 2 | mmu-miR-29b | 2.58 | 0.05 | hsa-miR-190b | 14.49 | 0 |
| 3 | mmu-miR-205 | 2.31 | 0.01 | mmu-miR-1928 | 7.85 | 0 |
| 4 | mmu-miR-130b* | 2.25 | 0.04 | hsa-miR-124* | 4.93 | 0 |
| 5 | mmu-miR-690 | 2.16 | 0.05 | mmu-miR-141 | 4.47 | 0 |
| 6 | mmu-miR-186 | −3.02 | 0 | mmu-miR-706 | 3.73 | 0 |
| 7 | mmu-miR-449a | −2.84 | 0.01 | mmu-miR-291a-3p | 3.67 | 0 |
| 8 | mmu-miR-331-5p | −2.44 | 0.01 | mmu-miR-1982.2 | 3.49 | 0 |
| 9 | rno-miR-632 | −25.01 | 0.03 | rno-miR-673 | 3.43 | 0.01 |
| 10 | mmu-miR-342-3p | −2.24 | 0.02 | mmu-miR-1896 | 3.32 | 0 |
| 11 | mmu-miR-376a* | −2.16 | 0.02 | hsa-miR-653 | 3.29 | 0.03 |
| 12 | mmu-miR-467b | −2.07 | 0.01 | mmu-miR-362-5p | 3.28 | 0.01 |
| 13 | mmu-miR-16 | −2 | 0.02 | mmu-miR-463* | 3.16 | 0.01 |
| 14 | hsa-miR-27b* | −2 | 0.01 | rno-miR-547 | 3.05 | 0.01 |
| 15 | | | | rno-miR-219-1-3p | 3.01 | 0.02 |
| 16 | | | | mmu-miR-146b | 2.93 | 0 |
| 17 | | | | mmu-miR-204 | 2.85 | 0.03 |
| 18 | | | | mmu-miR-300* | 2.84 | 0 |
| 19 | | | | mmu-miR-1188 | 2.83 | 0.01 |
| 20 | | | | mmu-miR-433-5p | 2.8 | 0 |
| 21 | | | | mmu-miR-200c | 2.79 | 0 |
| 22 | | | | mmu-miR-487b | 2.77 | 0 |
| 23 | | | | rno-miR-345-3p | 2.59 | 0 |
| 24 | | | | mmu-miR-130b* | 2.58 | 0 |
| 25 | | | | mmu-miR-363 | 2.51 | 0 |
| 26 | | | | rno-miR-409-3P | 2.49 | 0 |
| 27 | | | | mmu-miR-10a | 2.45 | 0 |
| 28 | | | | mmu-miR-342-3p | 2.42 | 0.01 |
| 29 | | | | mmu-miR-199b | 2.41 | 0 |
| 30 | | | | mmu-miR-28* | 2.38 | 0.01 |
| 31 | | | | mmu-miR-19b | 2.37 | 0 |
| 32 | | | | hsa-miR-28-3p | 2.36 | 0.02 |

TABLE 3-continued

| | | Amygdala Day 0 | | Amygdala Day 14 | | |
|---|---|---|---|---|---|---|
| S# | Detector | RQ_Stress-Control | P. Value Stress-Control | Detector | RQ_Stress-Control | P. Value Stress-Control |
| 33 | | | | hsa-miR-136* | 2.35 | 0.05 |
| 34 | | | | mmu-miR-124 | 2.35 | 0 |
| 35 | | | | mmu-miR-125b* | 2.32 | 0.03 |
| 36 | | | | mmu-miR-217 | 2.25 | 0.02 |
| 37 | | | | hsa-miR-412 | 2.23 | 0.01 |
| 38 | | | | hsa-miR-875-5p | 2.23 | 0.01 |
| 39 | | | | mmu-miR-674* | 2.22 | 0.02 |
| 40 | | | | mmu-miR-103 | 2.21 | 0 |
| 41 | | | | mmu-miR-671-3p | 2.19 | 0 |
| 42 | | | | hsa-miR-30e-3p | 2.18 | 0 |
| 43 | | | | mmu-miR-134 | 2.17 | 0.02 |
| 44 | | | | mmu-miR-223 | 2.16 | 0.03 |
| 45 | | | | rno-miR-146B | 2.14 | 0.01 |
| 46 | | | | mmu-miR-467b | 2.12 | 0 |
| 47 | | | | hsa-miR-421 | 2.1 | 0.01 |
| 48 | | | | mmu-miR-142-5p | 2.1 | 0 |
| 49 | | | | hsa-miR-151-5P | 2.09 | 0.02 |
| 50 | | | | hsa-miR-455 | 2.07 | 0 |
| 51 | | | | mmu-miR-9 | 2.06 | 0 |
| 52 | | | | mmu-miR-216b | 2.05 | 0 |
| 53 | | | | mmu-miR-99a | 2.05 | 0.03 |
| 54 | | | | rno-miR-344-3p | 2.04 | 0 |
| 55 | | | | hsa-miR-340 | 2.04 | 0 |
| 56 | | | | mmu-miR-383 | 2.03 | 0.01 |
| 57 | | | | mmu-miR-140 | 2.02 | 0 |
| 58 | | | | mmu-miR-188-5p | 2.01 | 0.02 |
| 59 | | | | hsa-miR-189 | 2 | 0.02 |
| 60 | | | | mmu-miR-322* | 2 | 0.01 |

Fourteen micro RNAs were modulated at day 0 whereas 60 micro RNAs were modulated at day 14 after the cessation of stress. It was also observed that most of the modulated micro RNAs at day 0 were significantly downregulated in both serum (27 out of 31) and amygdala (8 out of 14). However, this trend of micro RNA downregulation at day 0 was reversed at day 14 post stress where 78 out of 82 micro RNAs were upregulated in serum and all 60 significantly modulated micro RNAs were upregulated in amygdala. No common micro RNAs were found between all four groups. However, comparison of serum and amygdala profiles showed 9 common micro RNAs at Day 14. No similar micro RNAs between serum and amygdala were observed at day 0. Comparison of micro RNAs in serum samples at day 0 and 14 showed 18 common micro RNAs whereas only 4 micro RNAs were common in amygdala profiling data at day 0 and day 14 (FIG. 1). The symptoms and pathophysiology of PTSD in this model has been previously reported to develop at day 14 after stress exposure, which also correlates with the changes in the RNA expression profile. Moreover, PTSD in humans is shown to develop over a period of time after the traumatic stress (Jia et al., 2012). Therefore, micro RNA profiles of day 14 serum and amygdala were compared to diagnose PTSD in the stress animal model and 9 upregulated micro RNAs were identified as common viz., miR-142-5p, miR-19b, miR-1928, miR-223-3p, miR-322*, miR-324, miR-421-3p, miR-463* and miR-674* (Table 1). This panel of micro RNAs represented a small subset of micro RNAs, but it is nonetheless possible that the other serum micro RNAs could serve as biomarkers of traumatic stress, such as those presented in Table 2.

Example 6—Validation of Differential Expression in Taqman µRNA Assay

Figure 2:
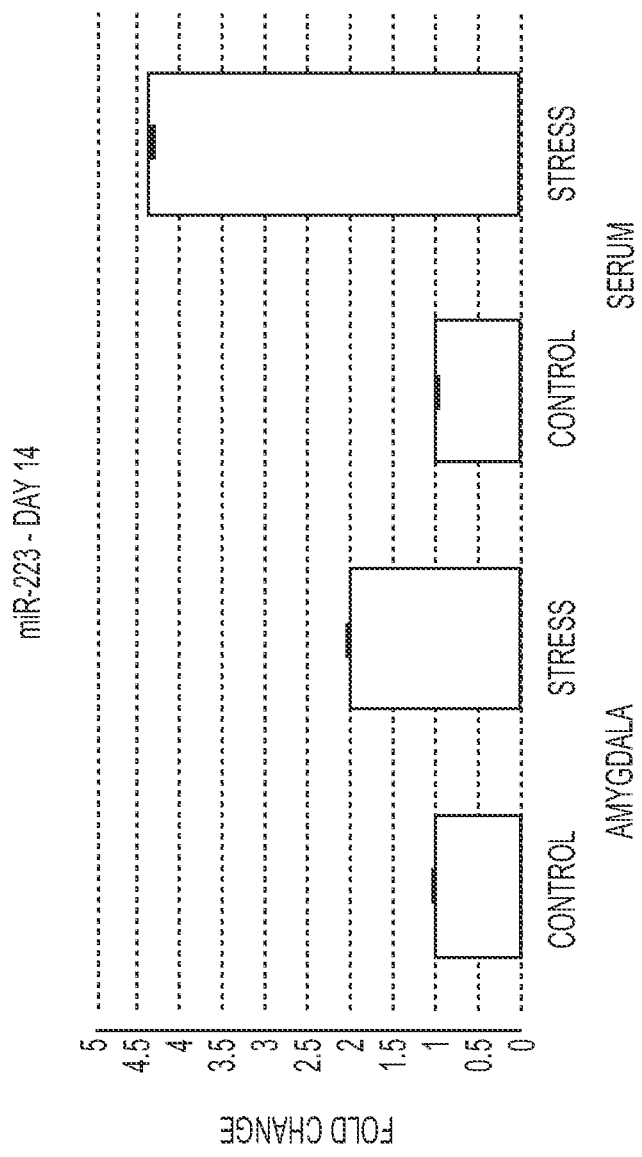
FIG. 2 illustrates overlapping micro RNAs data analysis for the modulated micro RNAs among the four traumatic stress groups was done using the online Venn diagram generation tool.
Figure 6:
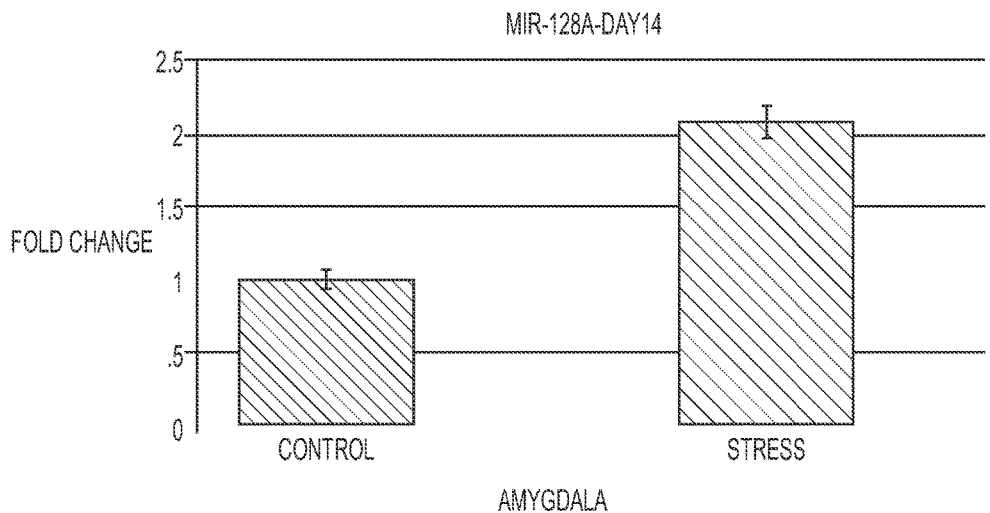
FIG. 6 illustrates validation of miR-128, expression in serum and amygdala samples of day 14. The levels of μRNA were normalized by the level of MammU6 endogenous control RNA, and all reactions were performed in triplicate.
Figure 7:
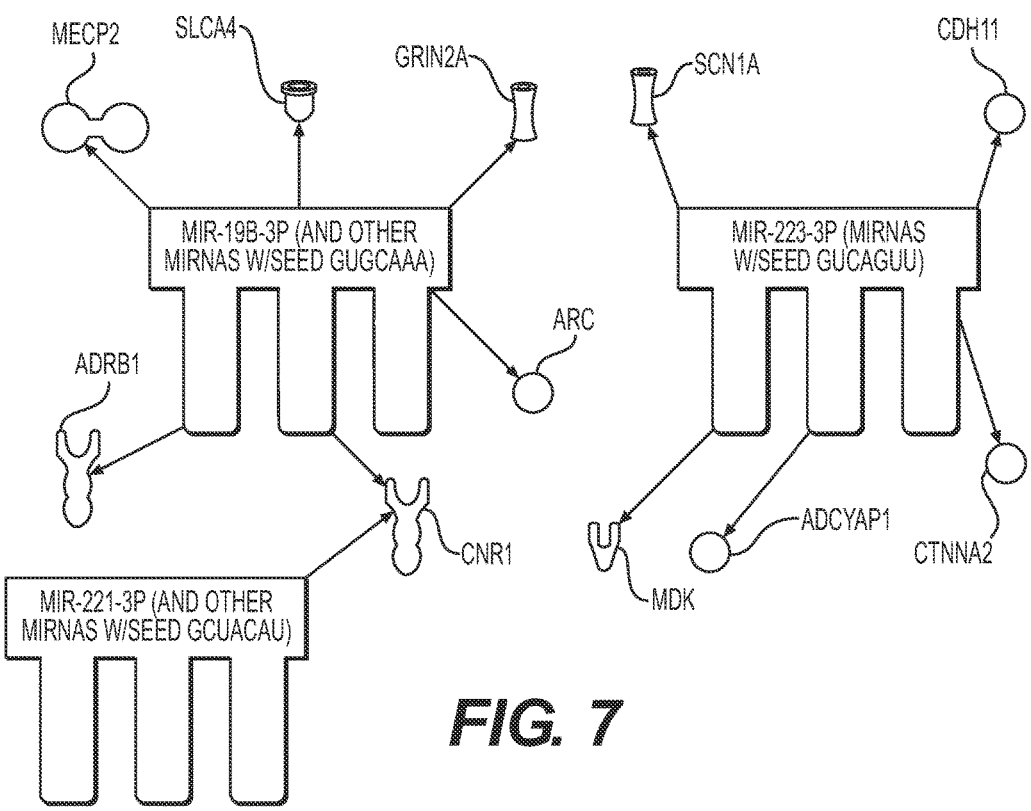
FIG. 7 illustrates network analysis of posttraumatic stress altered day 14 serum and amygdala common micro RNAs and their fear related gene targets based on published literatures and available in ingenuity pathway analysis (IPA) which identifies the relationship of μRNAs towards a specific pathway by predicting the binding affinity of a μRNA with the proteins of the pathway. In addition, it also used the current literature to identify the role of micro RNAs in a specific pathway. Three micro RNAs had a direct interaction with genes regulating the stress and fear response. These micro RNAs were identified as mir-19b-3p, mir-223-3p and mir-221-3p. Mir-19b and mir-223 regulate proteins involved in regulation of both fear and stress response

Global micro RNA screening platforms can introduce bias in the micro RNA profiling which can occur because of the reproducibility of the platform used, pre amplification step due to low serum concentration and stable endogenous controls. All these factors may contribute and lead to an identification of false positive (Balakathiresan et al., 2012). Therefore, validation of the micro RNA profiling data was obtained from low-density array platform by performing individual micro RNA assay. MiR-223 was selected as a representative for a validation study since it is reported that miR-223 is enriched in hippocampus, midbrain, and cortex (Harraz et al., 2012). MiR-223 is also implicated in studies related to brain injury and stroke, thus it is appreciated that the discovered micro RNA also detect TBI or Stroke, for which PTSD is usually co-morbid. MiR-223 is reported to be prevalent in the relatively large vessel-like structures scattered throughout the brain after TBI (Redell et al., 2009). In stroke animal model, miR-223 overexpression in hippocampus shows the neuroprotective effect by regulating the expression of glutamate receptor subunits, GluR2 and NR2B (Harraz et al., 2012). In this validation assay with miR-223, U6 small nucleolar RNA were chosen as an endogenous control. The singleplex PCR assay for miR-223 confirms and validates the expression for the same set of animals from the multiplex platform (FIG. 2). Validation of miR-128 expression in serum and amygdala samples of day 14 is also confirmed (FIG. 6).

Figure 3A:
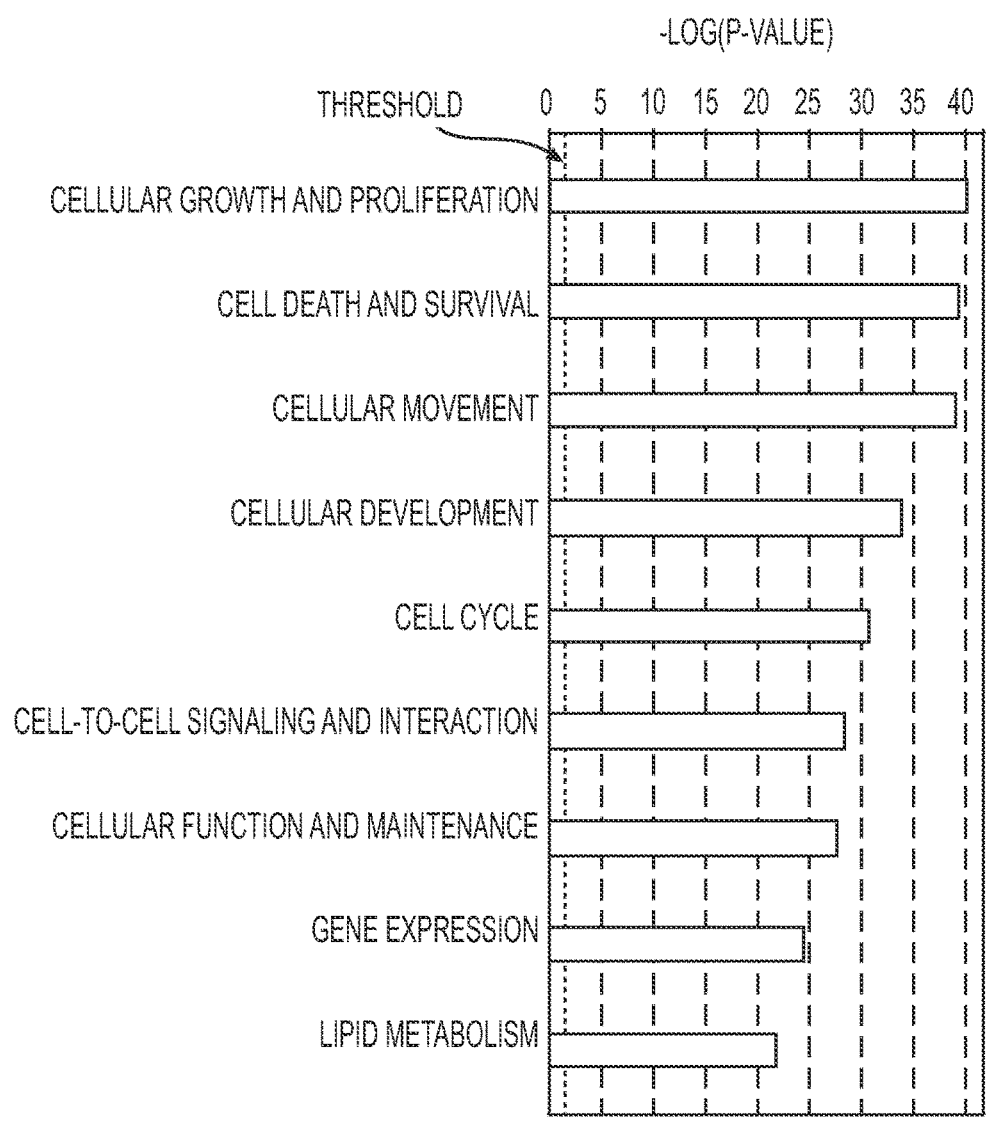
Figure 3B:
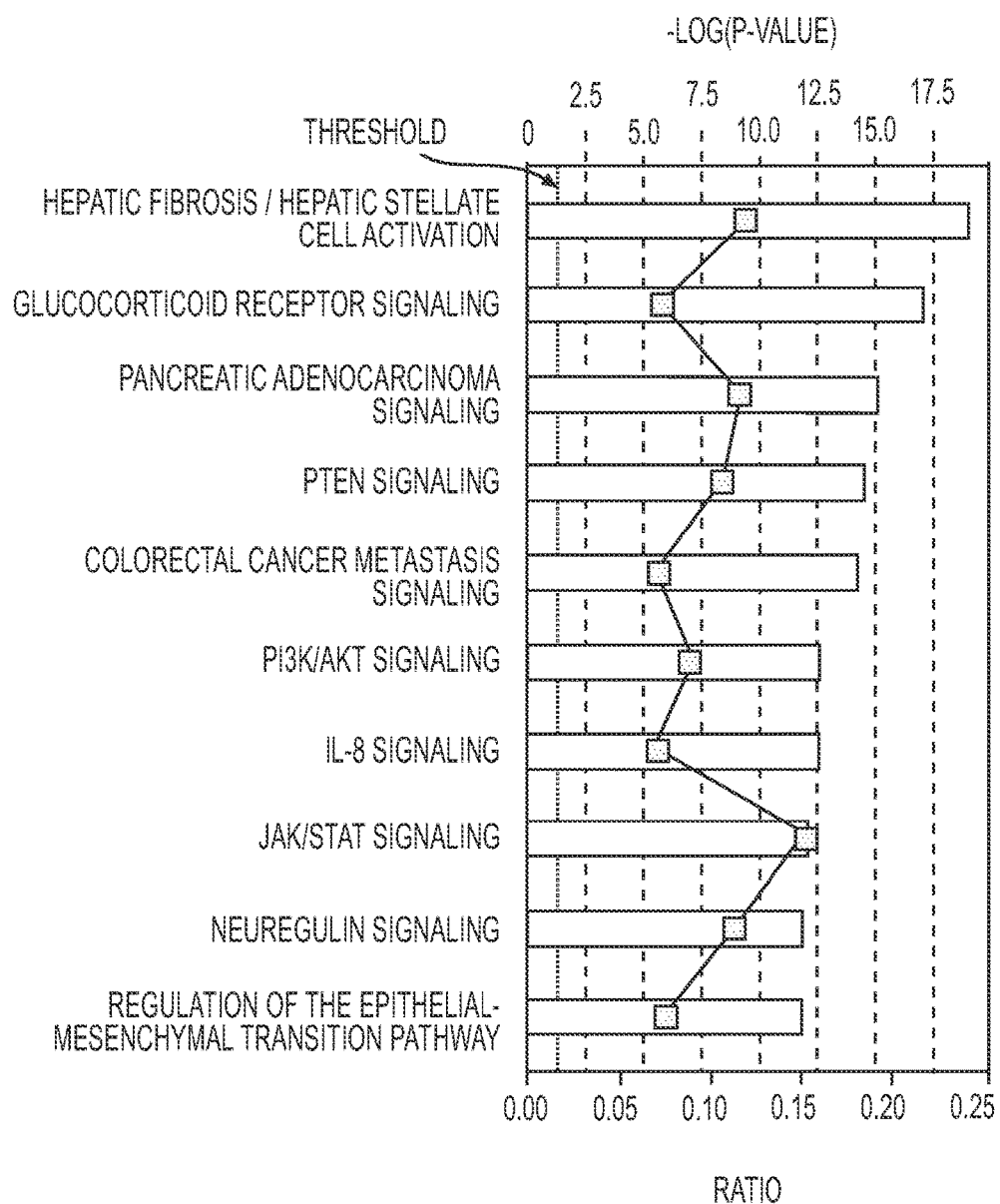
FIG. 3B illustrates the top 10 canonical pathways of posttraumatic stress altered day 14 serum and amygdala common micro RNAs and their validated targets from miR Walk database using Ingenuity pathway analysis program.
Figure 4:
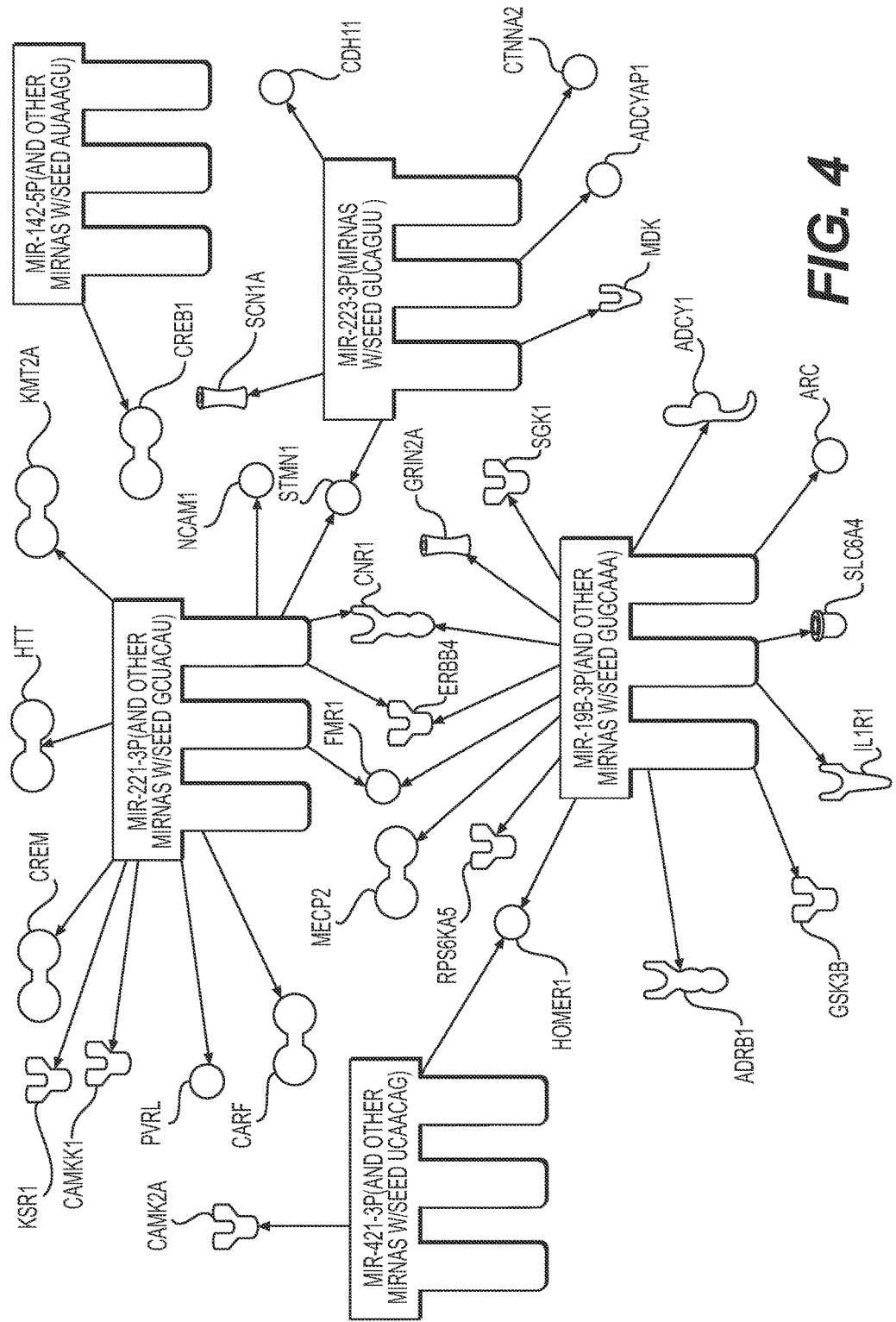
FIG. 4 illustrates network analysis of posttraumatic stress altered day 14 serum and amygdala common micro RNAs and their fear related gene targets based on published literatures and available in Ingenuity Pathway Analysis (IPA) software (Ingenuity Systems). The network correlation between micro RNAs and their targets relevant to fear response were custom-built using "my pathway" tool in IPA. Molecular functional network suggests that miR-223, miR-1928 (miR-221) may have direct role in STMN1 regulation.

Example 7—Prediction of Traumatic Stress Altered µRNA Targets and their Pathway Analysis To understand the role of the nine micro RNAs which are common to both serum and amygdala in PTSD pathophysiology, a bioinformatics analysis was performed to identify gene targets. Analysis in MiRWalk database showed 331 experimentally validated gene targets (Table 2). Among these genes, it can be found that genes involved in anxiety regulation or developments are among the targets of the modulated micro RNAs. Two genes stathmin 1 (STMN1) and aquaporin 4 (AQP4) were identified and the role of these two genes have been well-studied in anxiety disorder. Moreover, they have been identified as direct target of miR-223. Pathway analysis of validated gene targets by IPA program suggested cell death and survival as one of the top most biofunctions in the molecular and cellular functional category (FIG. 3A). In canonical pathways, glucocorticoid receptor signaling pathway was among the top five pathways which is regulated by micro RNAs (FIG. 3B). Molecular functional network was constructed using fear related genes and molecules suggested that miR-223, miR-1928 (miR-221) may have direct role in STMN1 regulation (FIG. 4). Taken together these data suggest that the selected nine micro RNAs have a role in PTSD development as their modulation was observed in both serum and amygdala and thus can serve as biomarkers.

The micro RNA expression at day 0 immediately after the cessation of stress showed that most of the micro RNAs were found to be downregulated in amygdala. Without being bound by any particular theory, this downregulation may be due to the "de novo protein synthesis" that supports long-lasting functional and structural plasticity which is a molecular requirement for new memory formation. (Griggs et al., 2013). The downregulated micro RNAs were also shown to regulate memory formation in amygdala by repressing actin-regulating proteins that are involved in plasticity and memory (Griggs et al., 2013). Furthermore, the global reduction of several micro RNAs expression in rodents forebrain such as amygdala, hippocampus and cortex have been shown to regulate learning and memory (Gao et al., 2010; Konopka et al., 2010; Lin et al., 2011; Griggs et al., 2013).

Much evidence indicates that the newly formed fear memories are being consolidated into stable long-term memories in the amygdala which are believed to be the site of fear memory storage (Fanselow et al., 1999; Nader et al., 2000). To identify the micro RNAs that are involved in consolidation and long-term stability of fear memories, micro RNA profiling was performed in amygdala at day 14 after the cessation of traumatic stress. Analysis of day 14 micro RNAs in amygdala revealed a substantial alteration of the posttranscriptional machinery characterized by a global increase in micro RNA expression. This change indicated the development and ongoing pathophysiology of the PTSD, as each microRNA was able to regulate the expression of several target genes (Beveridge et al., 2010). For example, it was observed two fold upregulation of miR-124, which has been shown to directly target mineralocorticoid receptor (MR) which regulates CORT secretion (Mannironi et al., 2013). Interestingly, Jia et al (2012) demonstrated the downregulation of MR in amygdala enhanced the secretion of CORT for several days and the development of anxiety. Due to the alteration of large number of micro RNAs (60 μRNAs; >2 fold) in day 14 amygdala, only those micro RNAs were selected that were common (9 micro RNAs) between serum and amygdala of day 14 for further analysis such as correlation with fear related genes. Network analysis of these 9 micro RNAs with their fear-related gene targets that are available in IPA showed only 5 of them were correlated with fear related genes (FIG. 4). For instance, cAMP responsive element binding protein 1 (Creb1) was identified as a direct target of miR-142-3p. Creb1 was recently reported to be down regulated in rat brain exposed to repeated inescapable shock (Smalheiser et al., 2011), suggesting that miR-142-3p may regulate the expression of Creb1 and may play an important role in stress related response (FIG. 4). Further, miR-221 and miR-223 were also found to regulate the expression of STMN1, an important amygdala molecule involved in fear conditioning (Shumyatsky et al., 2005).

IPA analysis suggested involvement of five micro RNAs viz., miR-142-5p, miR-19b, miR-1928, miR-223 and miR-421-3p in the regulation of genes associated with delayed and exaggerated fear. These five micro RNAs were explored for their brain specificity and/or their functions related to any neurological conditions. MiR-142-5p was found to be enriched in microglia and was shown to be upregulated after brain injury (Lei et al., 2009; Wu et al., 2011; Lau et al 2013). Further, auditory fear training in rats down regulated the expression of miR-142-5p in lateral amygdala of naïve animals, suggesting its involvement in memory formation dysfunction (Griggs et al., 2013). MiR-19b-3p that copurifies with polyribosomes in mammalian neurons show significantly higher expression in 6-hydroxydopamine-injured MN9D cells, indicating its role in neurodegenerative diseases by contributing to dopaminergic neuronal apoptosis (Li et al 2013). MiR-221-3p expression was also upregulated in distal axons of superior cervical ganglia (SCG) after spinal cord injury (Liu et al., 2009, Wu et al., 2011). MiR-223 and miR-19 were also enriched in glial cells and were shown to inhibit aberrant glial expression of neuronal proteins and phenotypes (Jovicid et al., 2013). The miR-421 was first identified in neocortex and hippocampus from developing rat brain and also plays a role in neurodegenerative disorders (Miska et al., 2004; Taguchi 2013). Recent studies also suggested participation of miR-421 in the regulation of plasminogen activator Inhibitor-1 (PAI-1) which is known to induce neuronal apoptosis, disrupt the blood-brain barrier (BBB) and contribute to neurotoxicity in ischemic brain damage after stroke (Abu Fanne et al., 2010; March-and et al 2012).

For biomarker identification, only day 14 serum micro RNA profiles were selected for the analysis, since the day 14 animals showed delayed and exaggerated startle response, enhanced plasma CORT and retarded body weight gain after several days (10-21 days) of posttraumatic stress in rats (Jia et al., 2012). Modulation of micro RNAs in serum can occur either because of the change in the micro RNAs expression in the regions of the brain which controls the stress response. These micro RNAs can leach out in the serum by different ways as previously described (Andrews and Neises 2012). However, there is a possibility that serum micro RNA modulation may occur due to a bystander effect of the stress on other organs which can potentially alter the serum micro RNA expression profile. Such micro RNAs can be a marker for organ stress but cannot be used as marker for psychological stress. To identify the true candidates biomarkers, micro RNA profiling was performed for amygdala which is believed to play a critical role in regulation of fear conditioning in this animal model (Andero et al., 2013). Nine micro RNAs that were upregulated in both amygdala and in serum were selected and analysed for their correlation with PTSD pathophysiology by computational analysis to validate their potential as diagnostic biomarkers of PTSD. Since micro RNA regulates the cell physiology by targeting the mRNA and altering the protein expression, the validated gene targets of the 9 candidate micro RNAs were identified using miRWalk program. These gene targets were used to identify the pathways involved using IPA. Interestingly, stress-related glucocorticoid receptor signalling pathway appeared as one of the major canonical pathway which was regulated by the 9 micro RNAs. These computational analyses suggest that the candidate biomarkers of PTSD have an important role in stress response and hence are good candidates for further biomarker validation studies.

Thus it is shown that traumatic stress associated with a global decrease in day 0 and global increase in day 14 in micro RNA expression in amygdala has profound psychopathological implications in the context of PTSD development by influencing genes involved in fear memory formation and consolidation. A panel of dysregulated micro RNAs present in both serum and amygdala after exposure to traumatic stress and their correlation with PTSD pathophysiology suggests them as promising candidates for biomarkers.

Example 8—Analysis of μRNAs in Serum for Biomarkers of PTSD

Altered expressions of serum and amygdala micro RNAs in an animal model of PTSD were examined. Differentially expressed and statistically significant micro RNAs in serum were validated for their presence in amygdala of corresponding animals. A panel of nine stress-responsive micro RNAs viz., miR-142-5p, miR-19b, miR-1928, miR-223-3p, miR-322*, miR-324, miR-421-3p, miR-463* and miR-674* were identified in serum at 14 days post exposure to traumatic stress. The animal model used induces enhanced fear response in the animals at day 14 which is evident from the increased startle response. Fear and stress both are the key features in PTSD diagnosis. Therefore, to identify putative serum biomarkers to diagnose PTSD, the role of these micro RNAs in both psychological stress and fear response were analyzed. The data was analyzed with ingenuity pathway analysis (IPA) which identifies the relationship of micro RNAs towards a specific pathway by predicting the binding affinity of a micro RNA with the proteins of the pathway. In addition, the current literature was also used to identify role of μRNAs in a specific pathway.

This analysis showed that among the nine micro RNAs 3 micro RNAs had a direct interaction with genes regulating the stress and fear response. These micro RNAs were miR-19b-3p, miR-223-3p and miR-221-3p. MiR-19b and miR-223 are found to regulate the proteins which are involved in regulation of both fear and stress response. Both of these molecules are found to regulate many proteins involved in stress and fear regulation. Among these, one protein which is common to these micro RNAs is adregenic receptor beta-1 (adrb-1). Volk et. al. (November 2014) reports, increased expression of miR-19b in amygdala which regulates the levels of adrb-1 regulate fear response. Direct correlation with the increased miR-19b expression in serum and amygdala is thus shown. In addition, the role of these micro RNAs is found in regulation of stathmin 1 which has been reported to play a crucial role in stress and fear response. Interaction of miR-221 with cnr-1, a molecule of stress responsive pathway, was found. Based on these analysis and other reports, it is clear that miR-19b-3p, miR-221-3p and miR-223-3p are involved in regulation of stress and fear responsive pathways and their appearance in serum post-traumatic stress is a direct results of the traumatic stress. Based on these results miR-19b-3p, miR-223-3p and miR221-3p are biomarkers of PTSD.

The trends in micro RNA levels detailed herein are found to correlate with other samples collected from human subjects, the samples including whole blood, cerebral spinal fluid (CSF), plasma, serum, urine, and saliva. miR-142-5p, miR-19b, miR-1928, miR-223-3p, miR-322*, miR-324, miR-421-3p, miR-463* and miR-674* levels were also confirmed to trend as detailed above. Thus animal data for PTSD, TBI and control groups performed in the Examples correlated with that of human subject who have been diagnosed with PTSD or a TBI, thus confirming the protocol as an animal model for human PTSD and TBI.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

Patent documents and publications mentioned in the specification are indicative of the levels of those skilled in the art to which the invention pertains. These documents and publications are incorporated herein by reference to the same extent as if each individual document or publication is specifically and individually incorporated herein by reference.

The invention claimed is:

1. A process for administering a therapeutic agent for treating post-traumatic stress disorder (PTSD), the process comprising:

measuring levels of miR-19b-3p, miR-223-3p and miR-221-3p micro RNA in a biological sample obtained at a first time point from a subject suspected of suffering from PTSD, comprising hybridizing agents that specifically hybridize to each of the micro RNA, amplifying each of the micro RNA and sequencing the micro RNA to confirm the identity of each of the micro RNA and quantifying the identified RNA, and administering a therapeutic for the treatment of PTSD based on the measurements of the micro RNA.

2. The process of claim 1 wherein said biological sample is obtained at least thirteen days after said subject has been exposed to traumatic event likely to cause PTSD.

3. The process of claim 1 wherein said biological sample is obtained within one week after said subject presents with clinical symptoms of PTSD.

4. The process of claim 1, wherein said biological sample is obtained within 24 hours after said subject presents with clinical symptoms of PTSD.

5. The process of claim 1 wherein said therapeutic agent is an antidepressant, an antipsychotic, or combinations thereof.

6. The process of claim 5, wherein said therapeutic is fluoxitine and paroxatine, venlafaxine, sertraline, mirtazapine, olanzapine and quetiapione, propranolol, or an $\alpha_1$-selective adrenoceptor antagonist, or combinations thereof.

7. The process of claim 1 wherein said biological sample is whole blood, plasma, serum, CSF, urine, saliva, sweat, prefrontal cortex tissue, hippocampus tissue, or ipsilateral cortex tissue.

* * * * *